(12) United States Patent
Rodgers et al.

(10) Patent No.: US 11,700,840 B2
(45) Date of Patent: *Jul. 18, 2023

(54) L-SERINE COMPOSITIONS, METHODS AND USES FOR TREATING NEURODEGENERATIVE DISEASES AND DISORDERS

(71) Applicant: THE INSTITUTE FOR ETHNOMEDICINE, Provo, UT (US)

(72) Inventors: Kenneth Rodgers, Sydney (AU); Rachael Dunlop, Sydney (AU); Paul A. Cox, Jackson Hole, WY (US)

(73) Assignee: THE INSTITUTE FOR ETHNOMEDICINE, Jackson, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/727,335

(22) Filed: Oct. 6, 2017

(65) Prior Publication Data
US 2018/0027781 A1    Feb. 1, 2018

Related U.S. Application Data

(63) Continuation of application No. 13/683,821, filed on Nov. 21, 2012, now abandoned.

(60) Provisional application No. 61/562,194, filed on Nov. 21, 2011.

(51) Int. Cl.
| | | |
|---|---|---|
| *A61K 31/198* | (2006.01) | |
| *A61K 38/00* | (2006.01) | |
| *A61K 31/195* | (2006.01) | |
| *A61P 25/28* | (2006.01) | |
| *A61P 25/00* | (2006.01) | |
| *A61P 25/16* | (2006.01) | |
| *A01K 67/027* | (2006.01) | |
| *A61P 43/00* | (2006.01) | |

(52) U.S. Cl.
CPC .......... *A01K 67/027* (2013.01); *A61K 31/198* (2013.01); *A61K 38/00* (2013.01); *A61P 25/00* (2018.01); *A61P 25/16* (2018.01); *A61P 25/28* (2018.01); *A61P 43/00* (2018.01)

(58) Field of Classification Search
CPC .......... A61P 25/28; A61P 25/16; A61P 25/00; A61P 11/00; A61P 21/00; A61P 25/18; A61P 43/00; G01N 2800/28; G01N 33/6896; A61K 31/198; A61K 38/00; A61K 47/64; A61K 47/542; A61K 9/0053
See application file for complete search history.

(56) References Cited

U.S. PATENT DOCUMENTS

| | | |
|---|---|---|
| 3,873,722 A | 3/1975 | Smythies |
| 4,491,589 A | 1/1985 | Dell et al. |
| 4,962,121 A | 10/1990 | Hamburger et al. |
| 7,256,002 B2 | 8/2007 | Cox et al. |
| 7,670,783 B2 | 3/2010 | Cox et al. |
| 7,901,895 B2 | 3/2011 | Cox et al. |
| 8,541,184 B2 | 9/2013 | Cox et al. |
| 8,603,753 B2 | 12/2013 | Cox et al. |
| 2004/0214873 A1 | 10/2004 | Herting |
| 2005/0042686 A1 | 2/2005 | Cox et al. |
| 2005/0287204 A1 | 12/2005 | Hageman et al. |
| 2006/0079542 A1 | 4/2006 | Nestor |
| 2007/0286909 A1 | 12/2007 | Smith et al. |
| 2007/0292893 A1 | 12/2007 | Cox et al. |
| 2008/0058395 A1 | 3/2008 | Heffernan et al. |
| 2008/0241121 A1 | 10/2008 | Salvemini |
| 2009/0048172 A1* | 2/2009 | Moessler ............. A61P 43/00 514/5.5 |

FOREIGN PATENT DOCUMENTS

| | | |
|---|---|---|
| EP | 0302624 A2 | 2/1989 |
| EP | 1004301 A1 | 5/2000 |
| JP | 2002-316929 A | 10/2002 |
| JP | 2007-520532 A | 7/2007 |
| WO | 199313034 A1 | 7/1993 |
| WO | 9501096 | 1/1995 |
| WO | 1999/04781 A | 4/1999 |
| WO | 1999052519 A2 | 10/1999 |
| WO | 2005/074910 A1 | 8/2005 |
| WO | 2005092325 A1 | 10/2005 |
| WO | 2008118785 A2 | 10/2008 |
| WO | 2010132128 A1 | 11/2010 |

(Continued)

OTHER PUBLICATIONS

Brand et al, "Cyanobacterial blooms and the occurrence of the neurotoxin, beta-N-methylamino-I-alanine (BMAA), in South Florida aquatic food webs," Harmful algae, vol. 9, No. 6, pp. 620-635 (Year: 2010).*

Wang et al. Neuroprotective Effect of L-serine against Temporary Cerebral Ischemia in Rats. Feb. 22, 2010. Journal of Neuroscience Research. vol. 88. pp. 2035-2045. (Year: 2010).*

Lumen. Nervous Tissue. Date retrieved: Apr. 2, 2021. <https://courses.lumenlearning.eom/boundless-ap/chapter/nervous-tissue/#:~:text=Nervous%20tissue%20is%20composed%20of,are%20six%20types%20of%20neuroglia.&text=Neurons%20are%20the%20other%20the,bodies%2C%20dendrites%2C%20and%20axons.> (Year: 2021).*

Kaplan et al. Alpha-Synuclein Its Biological Function and Role in Neurodegenerative Diseases. 2003. Journal of Molecular Neuroscience. vol. 20. pp. 83-92. (Year: 2003).*

(Continued)

*Primary Examiner* — Tracy Liu
(74) *Attorney, Agent, or Firm* — Pillsbury Winthrop Shaw Pittman LLP

(57) ABSTRACT

L-serine, L-serine precursors, L-serine derivatives and L-serine conjugates for treatment, amelioration and/or prevention of protein aggregation/tangles/plaques and diseases associated with protein aggregation/tangles/plaques. In particular, treatments and uses for L-serine, L-serine precursors, L-serine derivatives and L-serine conjugates include Alzheimer's disease (AD), Parkinson's disease, Amyotrophic Lateral Sclerosis (ALS), and Huntington disease (HD).

21 Claims, 14 Drawing Sheets

(56) References Cited

FOREIGN PATENT DOCUMENTS

WO    2011104298 A1    9/2011

OTHER PUBLICATIONS

Canadian Intellectual Property Office, Office Action for Canadian Patent Application No. 2,855,854, Oct. 31, 2018, pp. 1-10.
Benecke, "Beneficial Effects of L-Serine and Glycine in the Management of Seizures in 3-Phosphoglycerate Dehydrogenase Deficiency;" American Neurological Association; vol. 44; pp. 177-186; (1998).
Choi, Sung Hee, Patent Cooperation Treaty, International Searching Authority, KR, International Application No. PCT/US2012/066373, dated Feb. 27, 2013.
Cox et al.; "Cycad Neurotoxins, consumption of flying foxes, and ALS-PDC disease in Guam;" Neurology; vol. 58; No. 6; pp. 956-959; (2002).
De Koning, T.J., et al., Beneficial Effects of L-Serine and Glycine in the Managemen of Seizures in 3-Phosphoglycerate Dehydrogenase Deficiency, Annals of Neurology, 1998, 44(2):261-265.
Dunlop et al.; "The Non-Protein Amino Acid BMAA Is Misincorporated into Human Proteins in Place of L-Serine Causing Protein Misfolding and Aggregation;" PLOS One; vol. 8; Issue 9; 8 pages; (2013).
Hoffman et al.; "Hydroxamic Acids as a Novel Family of Serine Racemase Inhibitors: Mechanistic Analysis Reveals Different Modes of Interaction with the Pyridoxal-5'-phosphate Cofactor"; J. Med. Chem; vol. 52; pp. 6032-6041; (2009).
Holtcamp et al.; "The Emerging Science of BMAA—Do Cyanobacteria Contribute to Neurodegenerative Disease?" Environmental Health Perspectives; vol. 120; No. 3; 8 pages; (2012).
Komiya et al.; "Precise and short-time measurement method of mass diffusion coefficients;" Experimental Thermal and Fluid Science; vol. 30; No. 6; pp. 535-543; (2006).
Lemere et al., "Alzheimer's Disease Aβ Vaccine Reduces Central Nervous System Aβ Levels in a Non-Human Primate, the Caribbean Vervet," The American Journal of Pathology, 2004, 165(1):283-297.
Miller et al.; "Practice Parameter update: the care of the patient with amyotrophic lateral sclerosis: Drug, nutritional, and respiratory therapies (an evidence-based review): Report of the Quality Standards Subcommittee;" Neurology; vol. 73; pp. 1218-1226; (2009).
Moreno-Gonzalez, Misfolded Protein Aggregates: Mechanisms, Structures and Potential for Disease Transmission, Semin.Cell Dev. Biol., 2011, 22(5):482-487.
Murch et al.; "Occurrence of β-methylamino-L-alanine (BMAA) in ALS/PDC patients from Guam;" Acta Neurologia Scandinavica; vol. 110; pp. 267-269; (2004).
Ozawa et al.; "Translational incorporation of L-3,4-dihydroxyphenylalanine into proteins;" The FEBS Journal; vol. 272; No. 12; pp. 3162-3171; (2005).
Pablo et al. "Cyanobacterial neurotoxin BMAA in ALS and Alzheimer's disease;" Acta Neurologica Scandinavica; vol. 120; pp. 216-225; (2009).
European Patent Application No. 12851576.4; Supplementary European Search Report dated Dec. 11, 2015; 17 pages.
Nelson, Peter T., Correlation of Alzheimer Disease Neuropathologic Changes With Cognitive Status: a Review of the Literature, J_ Neuropathol. Exp. Neurol., May 2012, pp. 362-381, vol. 71(5).
European Molecular Biology Laboratory-European Bioinformatics Institute, "CHEBI:31524—droxidopa," Chemical Entities of Biological Interest, 6 pages, available at http://www.ebi.ac.uk/chebi/searchId.do?chebild=CHEBI%3A31524 (6 pages) (Last modified on Dec. 18, 2014 and accessed on Jun. 24, 2015).

* cited by examiner

L-SERINE COMPOSITIONS, METHODS AND USES FOR TREATING NEURODEGENERATIVE DISEASES AND DISORDERS

RELATED APPLICATIONS

This application is a continuation application of application Ser. No. 13/683,821, filed Nov. 21, 2012, which claims the benefit of priority to U.S. Application No. 61/562,194, filed Nov. 21, 2011, all of which applications are expressly incorporated herein by reference in their entirety.

INTRODUCTION

Protein translation is a highly efficient and accurate process for assembling the 20 standard amino acids into proteins. Error rates in translation are relatively rare (1 in $10^3$ to $10^4$) and rely on the ability of the system to discriminate between the 20 protein (or canonical) amino acids (Zaher, et al., *Cell* 136, 746-762 (2009)). However such rare errors which result in the mischarging of tRNA synthetase by the wrong amino acid can result in misfolded or truncated proteins, and subsequent cell damage, such as in the sti (sticky) mutation in mice where alanine is substituted for glutamic acid, resulting in neurodegeneration (Lee, et al., *Nature* 443, 50-55 (2006)). We here report that a nonprotein amino acid produced by cyanobacteria, β-methylamino-L-alanine (BMAA), can be mistakenly incorporated into human proteins. We also report that this misincorporation can be inhibited by L-serine.

Protein translation is the process whereby the genetic code is interpreted from information contained in the nucleic acid sequence in mRNA into the primary sequence of a polypeptide chain. Fidelity of protein synthesis, at the translational level, relies on the specificity of amino acid and cognate tRNA recognition by tRNA synthetases. In certain cases, when two protein amino acids have a similar structure, a proofreading step checks the "fit" of an amino acid to the catalytic site of the tRNA synthetase and the bond is hydrolysed if the wrong amino acid is bound (Zaher, et al., *Cell* 136, 746-762 (2009)). Hundreds of non-protein amino acids exist; many occur naturally in plants, some are produced in vivo from amino acid oxidation, others are synthetically produced (Rubenstein, et al. *Medicine (Baltimore)* 79, 80-89 (2000); Rodgers, et al., *Free Radic Biol Med* 32, 766-775 (2002); Rodgers, et al., *Int J Biochem Cell Biol* 40, 1452-1466 (2008); Bell, *J Agric Food Chem* 51, 2854-2865 (2003)). Nonprotein amino acids which are close structural analogues of any of the 20 protein amino acids can bind to an amino acid-tRNA synthetase and become mistakenly peptide bonded into a polypeptide chain (Rodgers, et al., *Int J Biochem Cell Biol* 40, 1452-1466 (2008)). In order to be incorporated into proteins, non-protein amino acids have to be present in the cell at sufficient levels to successfully compete with the protein amino acid for charging onto tRNA. Examples of non-protein amino acids which are misincorporated into proteins causing pathological effects include cavananine and L-DOPA (Rubenstein, et al. *Medicine (Baltimore)* 79, 80-89 (2000); Rodgers, et al., *Int J Biochem Cell Biol* 40, 1452-1466 (2008); Allende, et al., *J Biol Chem* 239, 1102-1106 (1964); Rosenthal, et al., *Science* 196, 658-660 (1977); Rosenthal *Quarterly Review of Biology*, 52, 155-178 (1977)).

BMAA has been found to be associated with proteins in cyanobacteria and other organisms (Banack, et al., *Mar Drugs* 5, 180-196 (2007); Cox, et al., *Proc Natl Acad Sci USA* 102, 5074-5078 (2005); Murch, et al., *Proc Natl Acad Sci USA* 101, 12228-12231 (2004)). The possibility that the cyanobacterial toxin BMAA is misincorporated into proteins was bolstered by a study in which autoradiographic analysis was performed on mice after a single injection of $^3$H-BMAA reported 'a distribution pattern similar to that of a protein-forming amino acid' (Karlsson, et al., *Pigment Cell Melanoma Res* 22, 120-130 (2009)). $^3$H-BMAA uptake was demonstrated in tissues with high levels of protein synthesis, and radioactivity was maintained in the tissue after acid extraction (Karlsson, et al., *Pigment Cell Melanoma Res* 22, 120-130 (2009)). These data are consistent with incorporation of BMAA by protein synthesis.

As disclosed herein, a nonprotein amino acid produced by cyanobacteria, β-methylamino-L-alanine (BMAA), can be mistakenly incorporated into human proteins. The misincorporation of BMAA can be inhibited by L-serine.

SUMMARY

As disclosed herein, L-Serine can block the insertion of BMAA in human cell cultures, preventing protein misfolding. Significantly, human cells that are at risk of undergoing programmed cell death via apoptosis can be rescued with the addition of L-Serine.

Alzheimer's Disease (AD) is a progressive neurodegenerative disease that impairs cognition and memory. The cause of this most common form of dementia is not known. There are familial and sporadic forms of Alzheimer's and known risk factors that affect the disease.

One of the hallmarks of Alzheimer's pathology is aggregated amyloid beta peptide (Aβ), along with other ubiquitinated and cytoskeletal proteinaceous materials. Aβ (predominantly 40 or 42 amino acids in length) is derived from the proteolytic cleavage of the full-length amyloid precursor protein (APP). APP is a membrane protein that contains Cu(II) and Zn(II) metal-ion binding sites in the tail portion that contains the Aβ region. Though Aβ containing plaques are part of the pathology of the disease, very little is known about the function of both this smaller peptide and the full-length APP. The plaque inducing 42-amino acid long Aβ protein is produced from the normal cleavage of APP into the various subforms. There are two pathways for APP shown in the figure at right, indicating the amyloidogenic path (left) to Aβ, sAPPβ and C99 or the non-amyloidogenic path (right) to p3, sAPPβ, and C83.

Accordingly, L-serine, as well as L-serine precursors, L-serine derivatives and L-serine conjugates, is a drug candidate for the treatment, amelioration and/or prevention of protein aggregation/tangles/plaques and diseases associated with protein aggregation/tangles/plaques such as Alzheimer's disease (AD), Parkinson's disease, Amyotrophic Lateral Sclerosis (ALS), Huntington's disease (HD) and as well as a treatment that can slow or stop disease progression or continuing neurodegeneration.

In accordance with the invention, there are provided methods and uses for L-serine, or a precursor, derivative or conjugate of L-serine in: preventing, inhibiting or reducing incorporation of β-N-methylamino-L-alanine (BMAA), or a derivative or isomer of BMAA, into one or more proteins of a mammalian cell; and preventing, inhibiting or reducing misfolding or aggregation of one or more proteins in a mammalian cell. In one embodiment, a method or use includes contacting a cell with L-serine, or a precursor, derivative or conjugate of L-serine, in an amount sufficient to prevent, inhibit or reduce incorporation of β-N-methyl-amino-L-alanine (BMAA), or a derivative or isomer of BMAA, into the protein. In another embodiment, a method or use includes contacting the cell with L-serine, or a precursor, derivative or conjugate of L-serine, in an amount sufficient to prevent, inhibit or reduce misfolding or aggregation of the protein.

In accordance with the invention, there are also provided methods and uses for L-serine, or a precursor, derivative or conjugate of L-serine in: reducing or decreasing risk of a neurological disease or disorder caused or characterized by misfolding or aggregation of one or more proteins in a subject; stabilizing, or reducing or inhibiting progression of, a neurological disease or disorder caused or characterized by misfolding or aggregation of one or more proteins in a subject; and treating a neurological disease or disorder caused or characterized by misfolding or aggregation of one or more proteins in a subject. In one embodiment, a method or use includes administering to the subject L-serine, or a precursor, derivative or conjugate of L-serine, in an amount sufficient to reduce or decrease risk of the neurological disease or disorder caused or characterized by misfolding or aggregation of one or more proteins. In another embodiment, a method or use includes administering to the subject L-serine, or a precursor, derivative or conjugate of L-serine, in an amount sufficient to stabilize, or reduce or inhibit progression of, a neurological disease or disorder a caused or characterized by misfolding or aggregation of one or more proteins. In a further embodiment, a method or use includes administering to the subject L-serine, or a precursor, derivative or conjugate of L-serine, in an amount sufficient to treat the neurological disease or disorder caused or characterized by misfolding or aggregation of one or more proteins.

Cells include mammalian, such as primate (e.g., human) cells. Particular non-limiting examples of cells include a neuron or a glial cell. Particular non-limiting examples of proteins include a TAR DNA-binding protein 43 (TDP-43) and alpha-synuclein.

Precursors, derivatives and conjugates of L-serine include an L-serine polymer (polyserine), a salt of L-serine, an alkylated L-serine or an L-serine lipid. Precursors, derivatives and conjugates of L-serine also include salts, such as a sodium salt, a potassium salt, a calcium salt, a magnesium salt, a zinc salt, or an ammonium salt of L-serine. Precursors, derivatives and conjugates of L-serine further include an alkylated L-serine, such as L-serine with an alkyl group, e.g., an alkyl comprising 1-20 carbon atoms. Precursors, derivatives and conjugates of L-serine moreover include an L-serine ester, an L-serine di-ester, a phosphate ester of L-serine, a sulfate or sulfonate ester of L-serine, a pegylated L-serine, a lipidated L-serine or an L-serine with one or more polyethylene glycol (PEG) moieties. A non-limiting example of a precursor of L-serine is L-phosphoserine.

Precursors, derivatives and conjugates of L-serine can be formulated into a composition or formulation, such as a pharmaceutical composition or formulation. Precursors, derivatives and conjugates of L-serine can also be included in liposomes or micelles. Such compositions and formulations, including pharmaceutical compositions, formulations, liposomes and micelles, include those suitable for administration or delivery by any route, such as orally, by injection, by infusion, by intubation, via catheter, intraspinally, or intracranially.

Derivatives and isomers of BMAA include, but are not limited to, 2,4-diaminobutyric acid (2,4-DAB), 2,3-diaminobutyric acid (2,3-DAB), N-(2-aminoethyl)glycine (AEG), or β-amino-N-methyl-alanine (BAMA).

Neurological diseases and disorders include diseases and disorders characterized by protein misfolding or protein aggregates, for example, histologically. Neurological diseases and disorders include diseases and disorders also include those characterized by motor or cognitive deficiency. Specific clinical forms of neurological diseases and disorders treatable in accordance with the methods and uses herein include Alzheimer's disease, Parkinson's disease, Amyotrophic Lateral Sclerosis (ALS), Progressive Supranuclear Palsy (PSP), Lewy Body Dementia (LBD), Amyotrophic Lateral Sclerosis/Parkinsonism Dementia Complex (ALS/PDC), Huntington's disease (HD), Pick's disease and Frontotemporal Dementia (FTD).

Non-limiting examples of a symptom of a neurological disease or disorder include, for example, motor or cognitive deficiency; fatigue; tremors; ataxia; slurred, thick or irregular speech; muscle cramps, twitching, atrophy or weakness; shortness of breath; eating, breathing or swallowing difficulty; short term or long term memory loss; difficulty concentrating or completing familiar or routine tasks; space and time confusion; vision, color or sign recognition loss; depth perception loss, speaking or writing difficulty; loss of judgment; vocabulary loss; moodiness; irritability; aggression; paranoia; delusions; withdrawal from social engagement; stiffness or rigidity; loss of fine or gross motor control; slowing of movement; impaired balance; body instability; posture or gait abnormality; shuffling walk; reduced coordination; physical instability; unsteady gait; motor dysfunction; jerky body movement; slowed saccadic eye movement; body rigidity; seizure; difficulty chewing, eating, swallowing or speaking; deterioration in cognition/mental capabilities; dementia; sleep, behavioral or psychiatric abnormalities; difficulty in speech or thinking; behavioral changes; impaired regulation of social conduct; passivity; lethargy; social withdrawal; inertia; over-activity; pacing; wandering; loss of balance; lunging forward when mobilizing; fast walking; imbalance (e.g., bumping into objects or people); falls; changes in personality; slowing of movement; loss of inhibition or ability to organize information; slurred speech; difficult swallowing; opthalmoparesis or impaired eye movement; impaired eyelid function; facial muscle contracture; Neck dystonia or backward tilt of the head with stiffening of neck muscles; sleep disruption; urinary/bowel incontinence; or parkinsonism.

Methods and uses of the invention include those that provide a subjective or objective improvement in any symptom of a neurological disease or disorder, as set forth herein, or that is known to one of skill in the art. In particular embodiments, a method or use prevents, reduces or inhibits onset, severity, frequency, or duration of one or more symptoms of a neurological disease or disorder.

Methods and uses of the invention include administration, delivery or contact of a subject, or any tissue organ or cell of a subject, with any compatible means for delivery or contact of L-serine, precursor, derivative or conjugate of L-serine. In particular embodiments, L-serine, precursor, derivative or conjugate of L-serine, is administered orally, by injection, by infusion, by intubation, via catheter or intracranially to a subject in a method or use. In more particular aspects, L-serine, precursor, derivative or conjugate of L-serine, is administered at least once daily for at least one week to a subject; at least two, three, four, five, six, seven, 8, 9, 10, 11 or 12 weeks to a subject or at least one, two, three, four, five, six, seven, 8, 9, 10, 11 or 12 months to a subject.

Methods and uses of the invention include doses of L-serine, precursor, derivative or conjugate of L-serine, optionally intended to achieve a desired effect. In particular embodiments, L-serine, precursor, derivative or conjugate of L-serine, is administered at a dose of about 1-10 mg/day, 10-25 mg/day, 25-50 mg/day, 50-100 mg/day, 100-250 mg/day, 250-500 mg/day, 500-750 mg/day, 750-1,000 mg/day, 1,000-2,000 mg/day, 2,000-3,000 mg/day, 3,000-4,000 mg/day, 4,000-5,000 mg/day, 5,000-7,500 mg/day, 7,500-10,000 mg/day, 10-15 g/day, 15-20 g/day, 20-25 g/day, 25-30 g/day, 30-40 g/day, 40-50 g/day 50-75 g/day or 75-100 g/day to a subject; is administered at a dose of about 1-10 mg/kg body weight, 10-25 mg/kg body weight, 25-50 mg/kg body weight, 50-100 mg/kg body weight, 100-250 mg/kg body weight, 250-500 mg/kg body weight, 500-750 mg/kg body weight, or 750-1,000 mg/kg body weight to a subject; or is administered at a dose of about 1-10 mg/kg body weight per day, 10-25 mg/kg body weight per day, 25-50 mg/kg body weight per day, 50-100 mg/kg body weight per day, 100-250 mg/kg body weight per day, 250-500 mg/kg body weight per day, 500-750 mg/kg body weight per day, or 750-1,000 mg/kg body weight per day to a subject.

The invention also provides methods for identifying an agent that reduces, inhibits or prevents incorporation of β-N-methylamino-L-alanine (BMAA), or a derivative or isomer of BMAA, into a protein. In one embodiment, a method includes contacting a serine racemase with a test compound in the presence of L-serine under conditions where the L-serine would be converted to D-serine by the serine racemase; and determining if the test compound inhibits or reduces conversion of the L-serine to D-serine by the serine racemase. If the test compound inhibits or reduces conversion of the L-serine to D-serine by the serine racemase the test compound is identified as an agent that reduces or inhibits or prevents incorporation of β-N-methylamino-L-alanine (BMAA), or a derivative or isomer of BMAA, into a protein.

The invention further provides methods for identifying a candidate agent for reducing or inhibiting or preventing incorporation of β-N-methylamino-L-alanine (BMAA), or a derivative or isomer of BMAA, into a protein. In one embodiment, a method includes contacting a serine racemase with L-serine under conditions where the L-serine would be converted to D-serine by the serine racemase in the presence of a test agent; and determining if the test agent inhibits or reduces conversion of the L-serine to D-serine by the serine racemase. An inhibition or reduction identifies the test agent as a candidate agent for reducing or inhibiting or preventing incorporation of β-N-methylamino-L-alanine (BMAA), or a derivative or isomer of BMAA, into a protein.

The invention moreover provides methods of screening for an agent that reduces or inhibits or prevents incorporation of β-N-methylamino-L-alanine (BMAA), or a derivative or isomer of BMAA, into a protein. In one embodiment, a method includes contacting a serine racemase with L-serine under conditions where the L-serine would be converted to D-serine by the serine racemase in the presence a test agent; and determining if the test agent inhibits or reduces conversion of the L-serine to D-serine by the serine racemase, thereby screening for an agent that reduces or inhibits or prevents incorporation of β-N-methylamino-L-alanine (BMAA), or a derivative or isomer of BMAA, into a protein.

DETAILED DESCRIPTION

Figure 1A:
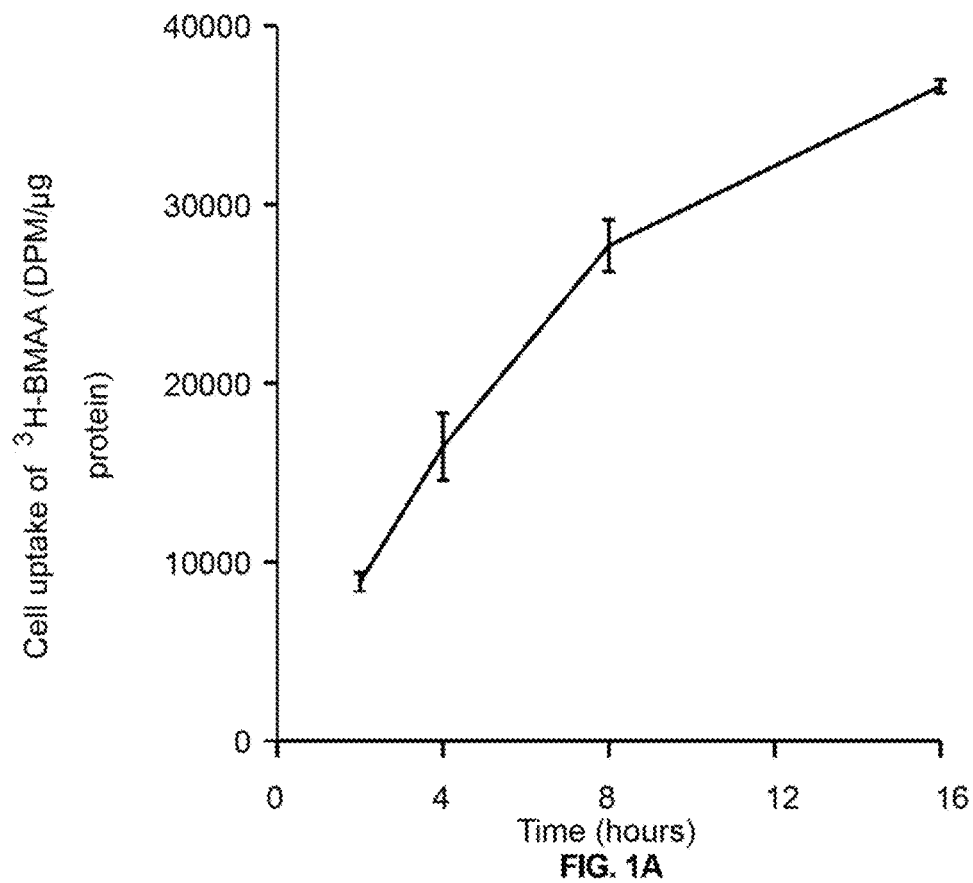
FIGS. 1A-1B show uptake and incorporation of $^3$H-BMAA into proteins by MRC-5 cells. MRC-5 cells were incubated with $^3$H-BMAA (31.25 nM) in HBSS containing 10% FCS. After 2, 4, and 16 hours, cells were lysed and the protein concentration and level of radioactivity in the lysate and cell proteins determined. 1A: Uptake of radiolabel by cells was expressed as disintegrations per minute (DPM) per µg of cell protein. 1B: Radiolabel in the cell protein fraction was expressed as DPM per µg of total cell protein

As disclosed herein, BMAA can be incorporated into proteins leading to undesirable protein misfolding, protein aggregation and consequent neuronal disorders and diseases characterized by protein aggregation/tangles/plaques. L-serine can inhibit or prevent BMAA incorporation into proteins thereby decreasing or preventing or undesirable protein aggregation and consequent neuronal disorders and diseases characterized by protein aggregation/tangles/plaques. Accordingly, L-serine, as well as L-serine precursors, L-serine derivatives and L-serine conjugates, can be used as a treatment for neuronal disorders and diseases characterized by protein aggregation/tangles/plaques.

In accordance with the invention, there are provided methods and uses for preventing, inhibiting or reducing incorporation of β-N-methylamino-L-alanine (BMAA), or a derivative or isomer of BMAA, into one or more proteins (e.g., present in a cell), and methods and uses for preventing, inhibiting or reducing misfolding or aggregation of one or more proteins of a cell (e.g., mammalian cell). In one embodiment, a method or use includes contacting a cell with L-serine, or a precursor, derivative or conjugate of L-serine, in an amount sufficient to prevent, inhibit or reduce incorporation of β-N-methylamino-L-alanine (BMAA), or a derivative or isomer of BMAA which mischarges serine aminoacyl-tRNA synthetase, into a protein of the cell (e.g., mammalian cell). Isomers of BMAA include 2,4-diaminobutyric acid (2,4-DAB), 2,3-diaminobutyric acid (2,3-DAB), N-(2-aminoethyl)glycine (AEG), and β-amino-N-methyl-alanine (BAMA) (Banack et al, *Toxicon* 56, 868-879 (2010); Banack et al, *Toxicon* 57, 730-738 (2011); Jiang et al, *Anal Bioanal Chem* 403, 1719-1730 (2012)). In another embodiment, a method or use includes contacting the cell with L-serine, or a precursor, derivative or conjugate of L-serine, in an amount sufficient to prevent, inhibit or reduce misfolding or aggregation of the protein of the cell (e.g., mammalian cell).

In accordance with the invention, there are also provided methods and uses for reducing or decreasing risk of a neurological disease or disorder caused or characterized by misfolding or aggregation of one or more proteins in a subject. In one embodiment, a method or use includes administering to the subject L-serine, or a precursor, derivative or conjugate of L-serine, in an amount sufficient to reduce or decrease risk of the neurological disease or disorder caused or characterized by misfolding or aggregation of one or more proteins.

In accordance with the invention, there are further provided methods and uses of stabilizing, preventing or reducing or inhibiting progression of, a neurological disease or disorder caused or characterized by misfolding or aggregation of one or more proteins in a subject. In one embodiment, a method or use includes administering to the subject L-serine, or a precursor, derivative or conjugate of L-serine, in an amount sufficient to stabilize, or reduce or inhibit progression of, a neurological disease or disorder a caused or characterized by misfolding or aggregation of one or more proteins.

In accordance with the invention, there are additionally provided methods and uses of treating a neurological disease or disorder caused or characterized by misfolding or aggregation of one or more proteins in a subject. In one embodiment, a method or use includes administering to the subject L-serine, or a precursor, derivative or conjugate of L-serine, in an amount sufficient to treat the neurological disease or disorder caused or characterized by misfolding or aggregation of one or more proteins.

Neurological disorders and diseases are characterized by abnormal or deficient nerve or neuron cell numbers, function or activity. Such nerve and neuron cells may be present in the central nervous system (CNS, e.g., brain, spinal cord) or peripheral nervous system (PNS, outside the brain and spinal cord, somatic, autonomic and sensory nervous system). Types of neurons affected by such disorders and diseases include unipolar, bipolar and multipolar (e.g., motor) neurons.

L-serine, as well as L-serine precursors, L-serine derivatives and L-serine conjugates, can provide a detectable or measurable therapeutic benefit or improvement to a subject. A therapeutic benefit or improvement is any measurable or detectable, objective or subjective, transient, temporary, or longer-term benefit to the subject or improvement in the disorder or disease, an adverse symptom, consequence or underlying cause, of any degree, in a tissue, organ, cell or cell population of the subject. Therapeutic benefits and improvements include, but are not limited to, reducing or decreasing occurrence, frequency, severity, progression, or duration of one or more symptoms or complications associated with a disorder or disease, or an underlying cause or consequential effect of the disorder or disease. L-serine, as well as L-serine precursors, L-serine derivatives and L-serine conjugates, methods and uses therefore include providing a therapeutic benefit or improvement to a subject.

Methods and uses of the invention include treatment methods and uses that desirably result in an improvement in a symptom or underlying cause of the subject's disease or disorder, that is a change considered beneficial to the subject. Thus, treatment can result in an improvement, such as inhibiting, reducing or preventing a progression or worsening of the disease or disorder or symptoms, or further deterioration or onset of one or more additional symptoms of the disease or disorder. Thus, a successful treatment outcome leads to a "therapeutic effect," or inhibiting, reducing or preventing the severity or frequency of one or more symptoms or underlying causes of a disease or disorder in the subject.

The term "ameliorate" means a detectable or measurable objective or subjective improvement in a subject's condition. A detectable or measurable improvement includes a subjective or objective reduction in the severity or frequency of one or more symptoms caused by or associated with the disorder or disease, or an improvement in the underlying causes of the disorder or disease, or a reversal of the disorder or disease.

Stabilizing a disease or disorder is also a successful treatment outcome. A successful treatment can reduce or prevent the severity or frequency of one or more symptoms of the disease or disorder, inhibit progression or worsening of the disease or disorder, and in some instances, reverse the disease or disorder. Accordingly, in the case of a neurological disease or disorder, for example, treatment can lead to an improvement of one or more symptoms of the neurological disease or disorder, stabilizing one or more symptoms of the neurological disease or disorder, or a reversal of the neurological disease or disorder.

Non-limiting symptoms of neurological disorders and diseases include, but are not limited to: motor (e.g., coordination) or cognitive deficiency; fatigue; tremors; ataxia; slurred, thick or irregular speech; muscle cramps, twitching, atrophy or weakness (e.g., hands, arms, legs, swallowing, breathing, speech muscles); shortness of breath; eating, breathing or swallowing difficulty. Non-limiting symptoms of neurological disorders and diseases also include, but are not limited to: short term or long term memory loss; difficulty concentrating or completing familiar or routine tasks; space and time confusion; vision, color or sign recognition loss; depth perception loss, speaking or writing difficulty; loss of judgment; vocabulary loss; moodiness; irritability; aggression; paranoia; delusions; and withdrawal from social engagement. Non-limiting symptoms of neurological disorders and diseases further include, but are not limited to: tremor; stiffness or rigidity; loss of fine or gross motor control; slowing of movement; impaired balance; body instability; posture or gait abnormality; and shuffling walk. Non-limiting symptoms of neurological disorders and diseases additionally include, but are not limited to: reduced coordination; physical instability; unsteady gait; motor dysfunction; jerky body movement (chorea); slowed saccadic eye movement; body rigidity; seizure; difficulty chewing, eating, swallowing or speaking; deterioration in cognition/mental capabilities including dementia; short and/or long term memory loss; sleep, behavioral and psychiatric abnormalities (e.g., anxiety, depression, loss of emotional affect, aggression, compulsory behavior). Non-limiting symptoms of neurological disorders and diseases moreover include, but are not limited to: difficulty in speech and thinking; behavioral changes; impaired regulation of social conduct (e.g. breaches of etiquette, tactlessness, dis-inhibition, criminal behavior); passivity; lethargy; social withdrawal; inertia; over-activity; pacing; wandering. Non-limiting symptoms of neurological disorders and diseases still further include, but are not limited to: loss of balance; lunging forward when mobilizing; fast walking; imbalance, e.g., bumping into objects or people; falls; changes in personality; slowing of movement; dementia (including loss of inhibition and ability to organize information); slurred speech; difficult swallowing; opthalmoparesis or impaired eye movement (particularly in the vertical direction which accounts for some of the falls experienced by patients); impaired eyelid function; facial muscle contracture; Neck dystonia or backward tilt of the head with stiffening of neck muscles; sleep disruption; urinary/bowel incontinence; and parkinsonism. Methods and uses, such as treatment in accordance with the invention, include treatment that improves or ameliorates any one of the foregoing symptoms, to any degree or duration of time.

Methods and uses, such as treatment in accordance with the invention, also include affecting the underlying causes of the disease or disorder thereof. Thus, in the case of a neurological disease or disorder, for example, stabilizing or decreasing worsening of the condition, for example, by objective and subjective measures of clinical severity of the neurological disorder is considered a successful treatment outcome. For example, the Amyotrophic Lateral Sclerosis Functional Rating Scale (ALSFRS) is a 10-item functional inventory devised for use in therapeutic Amyotrophic Lateral Sclerosis (ALS) trials. Functions such as eating, grooming, ambulation (motility and motor skills), communication and others are part of the scale. Accordingly, an improvement in the underlying cause of ALS can be reflected by an improvement in one or more of the functional inventories, for example.

In a method or use of the invention in which a therapeutic benefit or improvement is a desired outcome, L-serine, or a precursor, derivative or conjugate of L-serine, can be administered in a sufficient or effective amount to a subject in need thereof. An "amount sufficient" or "amount effective" refers to an amount that is calculated or likely to provide, in single or multiple doses, alone or in combination with one or more other compositions (therapeutic agents such as a chemotherapeutic or immune stimulating drug), treatments, or therapeutic protocols, regimens or agents, a detectable response of any duration of time (long or short term), a desired outcome in or a benefit to a subject of any measurable or detectable degree or for any duration of time (e.g., for hours, days, months, years, or cured). The dose or "sufficient amount" or "effective amount" for treatment (e.g., to provide a therapeutic benefit or improvement) typically is effective to ameliorate a disorder or disease, or one, multiple or all adverse symptoms, consequences or complications of the disorder or disease, to a measurable extent, although reducing or inhibiting a progression or worsening (e.g., stabilizing) of the disorder or disease or a symptom, is considered a satisfactory outcome.

Treatment can therefore result in inhibiting, reducing or preventing a disorder or disease, or an associated symptom or consequence, or underlying cause; inhibiting, reducing or preventing a progression or worsening of a disorder or disease, symptom or consequence, or underlying cause; or further deterioration or occurrence of one or more additional symptoms of the disorder or disease, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a disorder or disease, in the subject. Treatment methods and uses affecting one or more underlying causes of the disorder or disease or a symptom are therefore considered beneficial. Stabilizing or inhibiting or reducing progression or worsening of a disorder or disease is also a successful treatment outcome.

A therapeutic benefit or improvement therefore need not be complete ablation of any one, most or all symptoms, complications, consequences or underlying causes associated with the disorder or disease. Thus, a satisfactory endpoint is achieved even where only an incremental improvement in a subject's condition is achieved, such as a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the disease or disorder), of one or more of the physiological, biochemical or cellular manifestations or characteristics of the disorder or disease, over a short or long duration of time (minutes, hours, days, weeks, months, etc.).

A therapeutic benefit or treatment efficacy can be observed or measured by improvement in any one or more of the symptoms that characterize or are associated with the neurological disorder or disease a set forth herein. Particular non-limiting examples of therapeutic benefit or improvement for a neurological disorder or disease include, but is not limited to any of the following symptoms (e.g., a reduction or decrease of an adverse symptom or progression of an adverse symptom): motor (e.g., coordination) or cognitive deficiency; fatigue; tremors; ataxia; slurred, thick or irregular speech; muscle cramps, twitching, atrophy or weakness (e.g., hands, arms, legs, swallowing, breathing, speech muscles); shortness of breath; eating, breathing or swallowing difficulty; short term or long term memory loss; difficulty concentrating or completing familiar or routine tasks; space and time confusion; vision, color or sign recognition loss; depth perception loss, speaking or writing difficulty; loss of judgment; vocabulary loss; moodiness; irritability; aggression; paranoia; delusions; withdrawal from social engagement; tremor; stiffness or rigidity; loss of fine or gross motor control; slowing of movement; impaired balance; body instability; posture or gait abnormality; shuffling walk; reduced coordination; physical instability; unsteady gait; motor dysfunction; jerky body movement (chorea); slowed saccadic eye movement; body rigidity; seizure; difficulty chewing, eating, swallowing or speaking; deterioration in cognition/mental capabilities including dementia; short and/or long term memory loss; sleep, behavioral and psychiatric abnormalities (e.g., anxiety, depression, loss of emotional affect, aggression, compulsory behavior); difficulty in speech and thinking; behavioral changes; impaired regulation of social conduct (e.g. breaches of etiquette, tactlessness, dis-inhibition, criminal behavior); passivity; lethargy; social withdrawal; inertia; over-activity; pacing; wandering; loss of balance; lunging forward when mobilizing; fast walking; imbalance, e.g., bumping into objects or people; falls; changes in personality; slowing of movement; dementia (including loss of inhibition and ability to organize information); slurred speech; difficult swallowing; opthalmoparesis or impaired eye movement (particularly in the vertical direction which accounts for some of the falls experienced by patients); impaired eyelid function; facial muscle contracture; neck dystonia or backward tilt of the head with stiffening of neck muscles; sleep disruption; urinary/bowel incontinence; and parkinsonism. Methods and uses, such as treatment in accordance with the invention, include treatment that improves or ameliorates any one of the foregoing symptoms, to any extent or period of time.

Additional examples include measurement of various functions compared to established criteria. For example, an assessment of intellectual (cognitive) functioning such as memory testing or physical functioning can further characterize state of a disease. A therapeutic benefit or treatment efficacy of a neurological disorder or disease (or severity of a neurological disorder or disease) can also be ascertained or measured by mechanical means or instrumentation. In particular, positron electron tomography (PET) scan of the brain of a person with a neurological disorder or disease can show the degree to which there is a loss of function. Imaging such as computed tomography (CT) or magnetic resonance imaging (MRI), or with single positron emission computed tomography (SPECT) or positron emission tomography (PET) can also be used to identify cerebral pathology or subtypes of dementia in order to ascertain therapeutic benefit or treatment efficacy of a neurological disorder or disease, or severity of a neurological disorder or disease.

For Alzheimer's Disease (AD), a commonly used measure of cognitive impairment is the established NINCDS-ADRDA Alzheimer's Criteria for diagnosis. Eight cognitive domains are most commonly impaired in AD, namely, memory, language, perception (visual color, depth, symbol recognition), attention constructive/functional abilities, orientation and problem solving abilities. These domains can therefore be useful to ascertain diagnosis and as such any improvement of AD. A PET scan of the brain of a person with Alzheimer's disease classically shows biparietal hypometabolism in the temporal lobe.

For Amyotrophic Lateral Sclerosis (ALS, also known as Lou Gehrig's disease), diagnosis is primarily based on the symptoms and signs, and tests to rule out other diseases. A neurologic examination is used to assess whether symptoms such as muscle weakness, atrophy of muscles, hyper-reflexia, and spasticity are present, and over time, become progressively worse. One of these tests that distinguishes ALS from other diseases or disorders having similar symptoms is electromyography (EMG), a recording technique that detects electrical activity in muscles. Certain EMG findings can support the diagnosis of ALS. Another common test measures nerve conduction velocity (NCV). Specific abnormalities in NCV may suggest, for example, that the patient has a form of peripheral neuropathy (damage to peripheral nerves) or myopathy (muscle disease) rather than ALS. MRI scans are often normal in patients with ALS, but it can reveal evidence of other problems that may be causing the symptoms, such as a spinal cord tumor, a herniated disk in the neck, syringomyelia, or cervical spondylosis.

For Parkinson's Disease, diagnosis of onset can be made following the appearance of physical and/or psychological symptoms specific to the disease, as set for the herein, for example. Characteristic features include tremor; body stiffness or rigidity; loss of fine or gross motor control; slowing of movement; impaired balance; body instability; posture or gait abnormality; and shuffling walk, reduced coordination; physical instability; unsteady gait; motor dysfunction; jerky body movement (chorea); slowed saccadic eye movement; seizure; difficulty chewing, eating, swallowing or speaking; deterioration in cognition/mental capabilities including dementia; short and/or long term memory loss; sleep, and behavioral and psychiatric abnormalities (e.g., anxiety, depression, loss of emotional affect, aggression, compulsory behavior).

For Huntington's disease (HD), diagnosis of onset can be made following the appearance of physical and/or psychological symptoms specific to the disease, as set for the herein, for example. Excessive unintentional movements of any part of the body, which are abrupt and have random timing and distribution, suggest a diagnosis of HD. Cognitive or psychiatric symptoms are rarely the first diagnosed; they are usually only recognized in hindsight or when they develop further. Disease progression can be measured using the unified Huntington's disease rating scale which provides an overall rating based on motor, behavioral, cognitive, and functional assessments. Medical imaging, such as CT and MRI, can show atrophy of the caudate nuclei early in the disease, but these changes alone are not diagnostic of HD. Cerebral atrophy can be seen in the advanced stages of the disease. Genetic testing can be used to confirm a physical diagnosis if there is no family history of HD. Even before onset of symptoms, a genetic test can confirm if an individual carries an expanded copy of the trinucleotide CAG repeats in the HTT gene that causes the disease. Because HD follows an autosomal dominant pattern of inheritance, individuals who are at risk can be readily identified. A positive result can be obtained many years before symptoms begin. A negative test means that the individual does not carry the expanded copy of the gene and will not develop HD.

For Pick's Disease (PD), the most widely known criteria is from the UK Parkinson's Disease Society Brain Bank and the U.S. National Institute of Neurological Disorders and Stroke. The PD Society Brain Bank criteria requires slowness of movement (bradykinesia) plus either rigidity, resting tremor, or postural instability, while ruling out other possible causes for these symptoms. In addition, three or more of the following features are required during onset or evolution: unilateral onset, tremor at rest, progression in time, asymmetry of motor symptoms, response to levodopa for at least five years, clinical course of at least ten years and appearance of dyskenisias induced by the intake of excessive levodopa.

For Frontotemporal Dementia (FTD), diagnosis is primarily clinical including changed behaviors, changes in language, combined with neuropsychological tests and imaging. Structural MRI scans often reveal frontal lobe and/or anterior temporal lobe atrophy, but in early cases the scan may appear normal. Atrophy is often asymmetric. Comparison of images taken at different time points (e.g. a year apart) can show evidence of atrophy in two cross-sectional images that may be reported as normal. FDG-PET scans classically show frontal and/or anterior temporal hypometabolism, which also helps differentiate FTD from Alzheimer's disease.

An amount sufficient or an amount effective can but need not be provided in a single administration and, can but need not be, administered alone or in combination with another composition, treatment, protocol or therapeutic regimen. For example, the amount may be proportionally increased as indicated by the need of the subject, status of the disorder or disease treated or the side effects of treatment. In addition, an amount sufficient or an amount effective need not be sufficient or effective if given in single or multiple doses without a second composition, treatment, protocol or therapeutic regimen, since additional doses, amounts or duration above and beyond such doses, or additional compositions, treatments, protocols or therapeutic regimens may be included in order to be considered effective or sufficient in a given subject.

Amounts considered sufficient also include amounts that result in a reduction of the use of another treatment, therapeutic regimen or protocol. For example, a sufficient or effective amount of L-serine, or a precursor, derivative or conjugate of L-serine, is considered as having a therapeutic effect if administration results in less amount or frequency of a drug, or another therapy or protocol, being required to treat a neurological disorder or disease.

An amount sufficient or an amount effective need not be effective in each and every subject treated, prophylactically or therapeutically, in a particular subject, or a majority of treated subjects in a given group or population. As is typical for treatment or therapeutic methods, some subjects will exhibit greater or less response to a given treatment, therapeutic regimen or protocol. An amount sufficient or an amount effective refers to sufficiency or effectiveness in a given subject, not a group or the general population. Such amounts will depend in part upon the disease or disorder treated, such as the type or stage (early or advanced) of the disorder or disease, the therapeutic effect desired, as well as the individual subject (e.g., the bioavailability within the subject, gender, age, etc.).

An amount sufficient for the methods, uses and compositions of the invention include about 1-10 milligrams (mg), 10-25 mg, 25-50 mg, 50-100 mg, 100-250 mg, 250-500 mg, 500-750 mg, 750-1,000 mg, 1,000-2,000 mg, 2,000-3,000 mg, 3,000-4,000 mg, 4,000-5,000 mg, 5,000-7,500 mg, 7,500-10,000 mg, 10-15 grams (g), 15-20 g, 20-25 g, 25-30 g, 30-40 g, 40-50 g, 50-75 g or 75-100 g. Amounts sufficient can also be used according to the mass of a subject (e.g., in Kilograms, kg). For example, for a human subject, amounts of L-serine, or a precursor, derivative or conjugate of L-serine, include about 1-10 mg/kg body weight, 10-25 mg/kg body weight, 25-50 mg/kg body weight, 50-100 mg/kg body weight, 100-250 mg/kg body weight, 250-500 mg/kg body weight, 500-750 mg/kg body weight, 750-1,000 mg/kg body weight, 1-5 g/kg body weight, or 5-10 g/kg body weight of a subject. Such amounts for the methods, uses and compositions of the invention can be less, for example, from about 50-500, 500-5000, 5000-25,000 or 25,000-50,000 ng/kg.

Methods and uses of the invention may be practiced prior to (i.e. prophylaxis) or after symptoms begin, before or after symptoms or the disease or disorder develop. Administering L-serine, or a precursor, derivative or conjugate of L-serine, prior to or immediately following development of a symptom may decrease the severity or frequency of symptoms, or the underlying cause of the neurological disorder, in the subject. In addition, administering L-serine, or a precursor, derivative or conjugate of L-serine, prior to or immediately following development of one or more symptoms may stabilize or slow progression or worsening of a symptom, or the underlying cause of the neurological disorder or disease.

Methods and compositions of the invention may be used in vitro, ex vivo or in vivo. Compositions can be administered or delivered as a single or multiple dosage form, on consecutive or alternating days or intermittently, to a subject. For example, single or multiple dosage forms can be administered or delivered on alternating days or intermittently, over about 1 to 7, or 7 to 45, or 45 to 90 days or over about 1-4, 4-8, 8-12, 12-18, 18-24, 24-48, or more weeks, to a subject.

The term "contacting" means direct or indirect binding or interaction between two or more entities (e.g., between L-serine, a precursor, derivative or conjugate of L-serine, or molecule target, within a cell, for example). Contacting as used herein includes in solution, in solid phase, in vitro, ex vivo, in a cell and in vivo. Contacting in vivo can be referred to as administering, or administration, or in vivo delivery.

The term "subject" refers to animals, typically mammalian animals, such as a non-human primate (vervets, gorillas, chimpanzees, orangutans, macaques, gibbons), a domestic animal (dogs and cats), a farm animal (horses, cows, goats, sheep, pigs), experimental animal (mouse, rat, rabbit, guinea pig) and humans. Human subjects include adults and children. Human subjects include those having or at risk of having a neurological disorder. At risk subjects can be identified through genetic screening for predisposition towards a neurological disorder or a family history of a neurological disorder, for example, by accumulation of BMAA in keratinaceous tissues or blood plasma (see, e.g., U.S. Pat. Nos. 7,256,002 and 7,670,783). Subjects further include disease model animals (e.g., such as mice and non-human primates) for testing in vivo efficacy of L-serine, or a precursor, derivative or conjugate of L-serine.

The invention also provides compositions, including L-serine, or a precursor, derivative or conjugate of L-serine, in an amount that is able to produce one or more of the activities associated with L-serine. In one embodiment, a composition includes L-serine, or a precursor, derivative or conjugate of L-serine, in an amount sufficient to treat a neurological disorder. In another embodiment, a composition includes an amount of L-serine, or a precursor, derivative or conjugate of L-serine, sufficient to inhibit, reverse, ameliorate or reduce one or more symptoms of a neurological disorder. In yet another embodiment, a composition includes an amount of L-serine, or a precursor, derivative or conjugate of L-serine, sufficient to reverse an underlying causes of a neurological disorder.

Amounts of L-serine, or a precursor, derivative or conjugate of L-serine, for the methods, uses and compositions of the invention include about 1-10 milligrams (mg), 10-25 mg, 25-50 mg, 50-100 mg, 100-250 mg, 250-500 mg, 500-750 mg, 750-1,000 mg, 1,000-2,000 mg, 2,000-3,000 mg, 3,000-4,000 mg, 4,000-5,000 mg, 5,000-7,500 mg, 7,500-10,000 mg, 10-15 grams (g), 15-20 g, 20-25 g, 25-30 g, 30-40 g, 40-50 g, 50-75 g or 75-100 g. Amounts can also be produced and/or provided according to the mass of a subject (e.g., in Kilograms, kg). For example, for a human subject, amounts of L-serine, or a precursor, derivative or conjugate of L-serine can be adjusted according to the mass of the human. Such amounts of L-serine, or a precursor, derivative or conjugate of L-serine, include about 1-10 mg/kg body weight, 10-25 mg/kg body weight, 25-50 mg/kg body weight, 50-100 mg/kg body weight, 100-250 mg/kg body weight, 250-500 mg/kg body weight, 500-750 mg/kg body weight, 750-1,000 mg/kg body weight, 1-5 g/kg body weight, or 5-10 g/kg body weight of a subject. Such amounts can be less, for example, from about 50-500, 500-5000, 5000-25,000 or 25,000-50,000 ng/kg.

Methods and uses of the invention can be practiced using L-serine, or a precursor, derivative or conjugate of L-serine, optionally in such amounts as set forth herein. A derivative or conjugate of L-serine can be a modification (e.g., a protecting group) at any one, any two or all three functional groups, namely, the amino moiety ($NH_2$), acid moiety (—COOH) and/or the hydroxyl moiety (—OH) groups) of L-serine. The modified groups can be cleaved in vivo to yield free L-serine and a hydrolyzed protecting group. Suitable groups are pharmaceutically acceptable and typically substantially non-toxic. A derivative or conjugate of L-serine may have enhanced stability and/or solubility compared to free L-serine which aids in storage and dosing, and uptake of the L-serine active compound. These and other L-serine derivatives and conjugates known to one of skill in the art are included in the invention methods, uses and compositions (e.g., pharmaceutical formulations).

Non-limiting examples of L-serine derivatives and conjugates in which a hydroxyl moiety is derivatized to form a protected hydroxyl include ester, carbonate, phosphate, and sulfonate ester. The hydroxyl group of L-serine can be selectively esterified with a suitable carbonyl, phosphonyl, or sulfonyl electrophile after prior protection of the amino and acid moieties of the L-serine. Typically, one or both of the amino and acid protecting groups can be removed after selective esterification of the hydroxyl moiety; bio-compatibility of the acid and amino protecting groups is not an issue where both protecting groups are removed. Non-limiting examples of amino protecting groups include but are not limited to tert-butoxycarbonyl (Boc) and carbobenzyloxy (CBz), which are removable under acidic and hydrogenolysis conditions, respectively. Suitable acid protecting groups include tert-butyl (tBu) and benzyl (Bn) esters, which are removable under acidic and hydrogenolysis conditions, respectively. Suitable hydroxyl protection groups, are esters of carboxylic acids, phosphoric acid, phosphonic acids, sulfuric and sulfonic acids and other hydroxyl protecting groups known to the skilled artisan. One of ordinary skill in the art will appreciate that hydroxyl-protected L-serine may exist as a zwitterionic species as in the free amino acid or may be readily converted to a protic acid addition salt.

Non-limiting examples of L-serine derivatives and conjugates in which the amino moiety is derivatized include formation of an amide or urea, or carbamate-containing L-serine. The amino moiety of L-serine can be selectively derivatized after prior protection of the hydroxyl and acid moieties of the L-serine. Both hydroxyl and acid moieties in L-serine can be protected with groups amenable to removal after the final derivatization of the amino group. Typically, one or both of the hydroxyl and acid moiety protecting groups are removed after selective derivatization of the L serine amino moiety.

L-serine derivatives and conjugates include derivatization of the acid moiety, which can be selectively derivatized after protecting the hydroxyl and amino moieties of the L-serine. Both hydroxyl and amino moieties in L-serine can be masked with protecting groups that are amenable to removal after the final protection of the acid moiety. Typically, one or both of the hydroxyl and amino moiety protecting groups are removed after selective derivatization of the L-serine acid moiety.

In various additional embodiments, an L-serine conjugate includes a polymer. For example, L-serine can be within a small (e.g., 2-10) residue peptide which includes other amino acids. In this embodiment, enzymes such as peptidases and pepsin can cleave the peptide into individual amino acids, releasing L-serine. In such embodiments, the peptide can include two, three, four, five, six, seven, eight, nine, ten, 11, 12, 13, 14, 15, 16, 17, 18, 19, 20, etc., or more L-serine molecules Ser-[Ser]n where n is 1 to 1000. The administered peptide yields serine or smaller serine peptides which are in turned hydrolyzed.

Starting materials useful for preparing L-serine derivatives and conjugates are commercially available or can be prepared by well-known synthetic methods (Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al, "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesis of hydroxyl-protected serine compound and amino acid protection groups will be readily apparent to the skilled artisan.

L-serine, and precursors, derivatives and conjugates of L-serine, and compositions thereof (e.g., pharmaceutical formulations), may be administered systemically, regionally or locally by any route. For example, L-serine, or a precursor, derivative or conjugate of L-serine, may be administered intravenously, orally (e.g., ingestion), intracranially, intraspinally, intramuscularly, intraperitoneally, intradermally, subcutaneously, intracavity, transdermally (topical), parenterally, e.g. transmucosal and rectally. Methods, uses and -serine, and precursors, derivatives and conjugates of L-serine, and compositions thereof, of the invention including pharmaceutical formulations can be administered via a microencapsulated delivery system or packaged into an implant for sustained, continuous or intermittent administration.

Compositions further include pharmaceutical formulations containing L-serine, or a precursor, derivative or conjugate of L-serine. Such pharmaceutical formulations can be formulated in an amount having one or more of the activities disclosed herein, and a pharmaceutically acceptable carrier or excipient. In various embodiments, a pharmaceutical formulation includes L-serine, or a precursor, derivative or conjugate of L-serine in an amount sufficient to achieve an intended effect.

As used herein, the terms "pharmaceutically acceptable" and "physiologically acceptable" refer to carriers, excipients, diluents and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

A pharmaceutical formulation can be formulated to be compatible with its intended route of administration. Thus, pharmaceutical formulations include carriers, diluents, or excipients suitable for administration by routes including intraperitoneal, intradermal, subcutaneous, oral (e.g., ingestion or inhalation), intravenous, intracavity, intracranial, intraspinal, transdermal (topical), parenteral, e.g. transmucosal and rectal.

Solutions or suspensions used for parenteral, intradermal, or subcutaneous application can include the following: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical formulations suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can be included in the composition. Prolonged absorption of injectable formulations can be achieved by including an agent that delays absorption, for example, aluminum monostearate or gelatin.

For oral administration, L-serine, or a precursor, derivative or conjugate of L-serine, or composition thereof, can be incorporated with excipients in the form of tablets, troches, or capsules, e.g., gelatin capsules. Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidani such as colloidal silicon dioxide; a sweetening agent such as sucrose or saccharin; or a flavoring agent such as peppermint, methyl salicylate, or flavoring.

Formulations can also include carriers to protect L-serine, or a precursor, derivative or conjugate of L-serine against degradation or elimination from the body, such as a controlled release formulation, including materials that slowly degrade within the body and in turn release the active ingredient(s). For example, a time delay material such as glyceryl monostearate or glyceryl stearate alone, or in combination with a wax, may be employed.

Additional formulations include biodegradable or biocompatible particles or polymeric substances such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. Methods for preparation of such formulations are known to those skilled in the art. The materials can also be obtained commercially from Alza Corporation and Nova Pharmaceuticals, Inc., for example.

The rate of release of L-serine, or a precursor, derivative or conjugate of L-serine can be controlled by altering the concentration or composition of such macromolecules. For example, L-serine, or a precursor, derivative or conjugate of L-serine can be entrapped in microcapsules prepared by coacervation techniques or by interfacial polymerization, for example, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems including oil-in-water emulsions, micelles, mixed micelles, and liposomes. These can be prepared according to methods known the skilled artisan, for example, as described in U.S. Pat. No. 4,522,811.

Additional pharmaceutical formulations appropriate for administration are known in the art and are applicable in the methods, uses and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; and Pharmaceutical Principles of Solid Dosage Forms, Technonic Publishing Co., Inc., Lancaster, Pa., (1993)).

L-serine, or a precursor, derivative or conjugate of L-serine of the invention can include combinations of other compositions, and be included in the pharmaceutical compositions of the invention. For example, a drug that is used to treat a neurological disorder can be included with L-serine, or a precursor, derivative or conjugate of L-serine.

L-serine, or a precursor, derivative or conjugate of L-serine, including pharmaceutical formulations thereof can be packaged into kits, which optionally can contain instructions for use, for example, practicing a method or use of the invention. The invention therefore provides kits. In one embodiment, a kit includes L-serine, or a precursor, derivative or conjugate of L-serine, and/or a pharmaceutical formulation, packaged into suitable packaging material. In additional embodiments, a kit includes a label or packaging insert for practicing a method of the invention. Thus, in one embodiment, a kit includes instructions for treating a subject having or at risk of having a neurological disorder, in vitro, in vivo, or ex vivo. In additional embodiments, a kit includes a label or packaging insert including instructions for treating a subject having a neurological disorder in vivo, or ex vivo.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method or use of the invention. Kits of the invention therefore can additionally include instructions for using the kit components in a method or use of the invention.

Instructions can include instructions for practicing any of the methods or uses of the invention described herein. Thus, L-serine, or a precursor, derivative or conjugate of L-serine and pharmaceutical compositions thereof can be included in a container, pack, or dispenser together with instructions for administration to a subject. Instructions may additionally include indications, a satisfactory clinical endpoint, any adverse symptoms that may occur, or additional information required by the Food and Drug Administration for use on a human subject.

The instructions may be on "printed matter," e.g., on paper or cardboard within the kit, on a label affixed to the kit or packaging material, or attached to a vial or tube containing a component of the kit. Instructions may comprise voice or video tape which can optionally be included on a computer readable medium, such as a disk (hard disk), optical CD such as CD- or DVD-ROM/RAM, magnetic tape, electrical storage media such as RAM and ROM and hybrids of these such as magnetic/optical storage media.

Invention kits can also include one or more drugs that provide a synergistic or additive effect or that reduce or ameliorate one or more symptoms of a neurological disorder. For example, a drug that reduces or decreases a symptom of a neurological disorder may be included. Invention kits can additionally include a buffering agent, a preservative, or a stabilizing agent. The kit can further include control components for assaying an activity or effect of treatment. Each component of the kit can be enclosed within a separate individual container. For example, a kit can include a single unit dose of L-serine, or a precursor, derivative or conjugate of L-serine as set forth herein. Alternatively, a kit can include multiple unit doses of L-serine, or a precursor, derivative or conjugate of L-serine. For example, each of the multiple unit doses would contain an amount of L-serine, or precursor, derivative or conjugate of L-serine, in a separate individual container. Kit components can be in a mixture of one or more containers and all of the various containers can be within single or multiple packages.

The invention provides cell-free and cell-based methods of screening for, detecting and identifying agents that modulate serine racemase activity, and methods of screening, detecting and identifying agents that modulate incorporation of β-N-methylamino-L-alanine (BMAA), or a derivative or isomer of BMAA into a protein. The methods can be performed in solution, in solid phase, in silica, in vitro, in a cell, and in vivo.

In one embodiment, a method of screening for an agent includes contacting serine racemase under conditions allowing L-serine to be converted into D-serine in the presence a of test agent; and determining if the test agent inhibits or reduces conversion of L-serine into D-serine. In another embodiment, a method of identifying an agent that reduces or inhibits or prevents incorporation of β-N-methylamino-L-alanine (BMAA), or a derivative or isomer of BMAA, into a protein includes contacting a serine racemase with a test compound in the presence of a L-serine under conditions where the L-serine is converted to D-serine by the serine racemase and determining if the test compound inhibits or reduces conversion of the L-serine to D-serine by the serine racemase. A reduction or inhibition of serine racemase converting L-serine to D-serine in the presence of the test agent or test compound identifies the test agent or test compound as an agent that decreases, reduces or inhibits or reduces conversion of L-serine into D-serine, or that reduces or inhibits or prevents incorporation of β-N-methylamino-L-alanine (BMAA), or a derivative or isomer of BMAA, into a protein.

In a further embodiment, a method of identifying a candidate agent for reducing or inhibiting or preventing incorporation of β-N-methylamino-L-alanine (BMAA), or a derivative or isomer of BMAA, into a protein, includes contacting a serine racemase with L-serine under conditions where the L-serine would be converted to D-serine by the serine racemase in the presence of a test agent; and determining if the test agent inhibits or reduces conversion of the L-serine to D-serine by the serine racemase. An inhibition or reduction of D-serine identifies the test agent as a candidate agent for reducing or inhibiting or preventing incorporation of β-N-methylamino-L-alanine (BMAA), or a derivative or isomer of BMAA, into a protein.

In an additional embodiment, a method of screening for an agent that reduces or inhibits or prevents incorporation of β-N-methylamino-L-alanine (BMAA), or a derivative or isomer of BMAA, into a protein, includes contacting a serine racemase with L-serine under conditions where the L-serine would be converted to D-serine by the serine racemase in the presence a test agent; and determining if the test agent inhibits or reduces conversion of the L-serine to D-serine by the serine racemase. The foregoing method thereby screens for an agent that reduces or inhibits or prevents incorporation of β-N-methylamino-L-alanine (BMAA), or a derivative or isomer of BMAA, into a protein.

Such methods can include further or additional method steps. For example, methods of identifying, detecting and screening can include also measuring the activity of the agent to reduce or inhibit or prevent incorporation of β-N-methylamino-L-alanine (BMAA), or a derivative or isomer of BMAA into a protein in a cell.

The terms "determining," "assaying" and "measuring" and grammatical variations thereof are used interchangeably herein and refer to either qualitative or quantitative determinations, or both qualitative and quantitative determinations. When the terms are used in reference to measurement or detection, any means of assessing the relative amount, including the various methods set forth herein and known in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All patents, applications, publications, other references, GenBank citations and ATCC citations cited herein are expressly incorporated by reference herein in their entirety. In case of conflict, the specification, including definitions, will control.

As used herein, the singular forms "a", "and," and "the" include plural referents unless the context clearly indicates otherwise. Thus, for example, reference to "L-serine, or a precursor, derivative or conjugate of L-serine" includes a plurality of L-serine, or precursors, derivatives or conjugates of L-serine, and so forth.

As used herein, all numerical values or numerical ranges include integers within such ranges and fractions of the values or the integers within ranges unless the context clearly indicates otherwise. Thus, for example, reference to a range of 1-10, includes 1, 2, 3, 4, 5, etc., as well as 1.1, 1.2, 1.3, 1.4, 1.5, etc., 2.1, 2.2, 2.3, 2.4, 2.5, etc., and so forth. A reference to a range includes a reference to subranges within that range. Thus, for example, reference to 1-10 also include 1-3, 1-4, 1-5, 1-6, 2-4, 2-5, 2-6, 2-7, 3-5, 3-6, 3-7, 3-8, etc. Reference to a series of ranges, for example, reference to a range of 1-10 mg, 10-25 mg, 25-50 mg, 50-100 mg, 100-250 mg, 250-500 mg, 500-750 mg, 750-1,000 mg, 1,000-2,000 mg, 2,000-3,000 mg, 3,000-4,000 mg, 4,000-5,000 mg, 5,000-7,500 mg, 7,500-10,000 mg, 10-15 g, 15-20 g, 20-25 g, 25-30 g, 30-40 g, 40-50 g, 50-75 g and 75-100 g include combinations of combined ranges, such as 10-50, 50-500, 70-100 mg or g, etc. A series of ranges include both lower and upper ends of those ranges combined into ranges. Thus, for example, reference to a series of ranges such as 50-100 100-200, and 200-300, includes a range of 50-200, 50-300, 100-300, etc.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods.
Materials & Methods
MRC-5 cells were from American Tissue and Cell Culture (Va., USA). SH-SY5Y cells were from the European Collection of Cell Culture (ECACC). $^3$H-BMAA (80 Ci/mmol, 0.5 mCi/mL) was obtained from American Radiolabeled Chemicals. Dulbecco's modification of Eagle's minimum essential medium (DMEM) and HAMS F12 were from JRH biosciences, (Lenexa, Kans., USA). BMAA, dithiothreitol, L-serine, D-serine, acridine orange, ethidium bromide, cycloheximide and SDS were from Sigma Chemical Co. (Sigma-Aldrich, Castle Hill, NSW, Australia). BCA protein reagent was from Pierce Biotechnology (Rockford, Ill., USA). BD Pharminigen™ Annexin V-FITC apoptosis detection kit was from BD Biosciences (Sydney Australia). Water was from a Milli Q 4 stage system (Millipore-Waters, Lane Cove, NSW, Australia). All HPLC equipment was supplied by the Shimadzu Corporation (Kyoto, Japan) except the column (Nova-Pak® C18 4 µM 3.9×300 mm) and the AccQ•Tag derivitization kit which were supplied by Waters Corporation (Mass., USA). Other chemicals, solvents and chromatographic materials were AR or HPLC grade.

Cell Culture

MRC-5 cells, a human lung fibroblast cell line (passage number 14-19), and SH-SY5Y cells, a human neuroblastoma cell-line (passage number 30-32), were maintained in DMEM, or DMEM/Hams F12 respectively containing 10% fetal bovine serum (FBS), 4 mM L-glutamine, 100 U/mL penicillin, and 100 µg/mL streptomycin at 37° C. in a humidified atmosphere of 5% CO2 and 95% air. Human umbilical vein endothelial cells (HUVEC) were harvested enzymatically with type II collagenase (Sigma-Aldrich) under sterile conditions as described by Minter (Minter, et al., *Thromb Haemost* 67, 718-723 (1992)) and established as primary cell cultures in M199 (Trace Biosciences, Sydney, Australia) containing 20% FBS, 4 mM L-glutamine, 0.5% endothelial cell growth promoter, 100 U/mL penicillin, and 100 µg/mL streptomycin. All media were prepared with endotoxin-free water (Baxter) and filtered with Zetapore filters (Cuno Life Sciences Division). Cells were seeded at $3 \times 10^5$ cells per well in 6 well plates and allowed to adhere overnight (16 hours) before treatment.

Studies Examining Incorporation of BMAA into Proteins and Inhibition of Incorporation by Cycloheximide and Amino Acids MRC-5 cells were incubated with $^3$H-BMAA (31.25 nM) in HBSS containing 10% FCS. After 2, 4, and 16 hours, cells were washed three times in phosphate buffered saline and lysed by freeze-thawing in Triton X-100. The protein concentration in the lysate was determined using the bicinchoninic acid assay (BCA) (Smith, et al., *Anal Biochem* 150, 76-85 (1985)) (and radiolabel in the cell lysate quantified by liquid scintillation counting (LSC). Cell proteins were then isolated by trichloroacetic acid (TCA) (5%) precipitation washed three times in TCA (5%) and dissolved in formic acid.

To determine if incorporation of radiolabel into proteins was protein synthesis dependent MRC-5, SH-SY5Y and HUVEC cells were incubated with $^3$H-BMAA (31.25 nM) with or without CHX 2 µg/ml for 16 hours. The amount of radiolabel present in cell proteins in the CHM-treated cultures was expressed relative to that of control cultures, which was set at 100%. Parallel cultures of MRC-5 cells were incubated with $^3$H-leucine (41 nM) with or without CHX 2 µg/ml under identical culture conditions and processed as before.

To examine the ability of individual amino acids to reduce incorporation or radiolabel into proteins, MRC-5 cells were incubated with $^3$H-BMAA (31.25 nM) for 16 hours in the presence of individual amino acids (250 µM) and the radiolabel present in the cell proteins assessed as before. All of the 20 protein amino acids (L-isomers) were examined individually in triplicate cell cultures. To confirm that L-serine had an inhibitory effect on incorporation of radiolabel into proteins, MRC-5 cells were incubated with $^3$H-BMAA (31.25 nM) for 16 hours in the presence of L-serine (0, 50, 100 and 250 µM) and in a separate experiment with 250 µM L-serine and D-serine. Incorporation of radiolabel was determined relative to cells incubated in medium containing no serine. MRC-5 cells were then incubated with $^3$H-BMAA (31.25 nM) for 16 hours in HBSS alone, HBSS containing all 20 protein amino acids (400 µM) or 19 protein amino acids except L-serine and the amount of radiolabel in cell protein assessed as before.

Removal of Radiolabel from Cell Proteins Generated by Incubating MRC-5 Cells with 3H-BMAA SH-SY5Y cells were incubated with $^3$H-BMAA (31.25 nM) for 24 hours and cell proteins isolated by TCA (5%) precipitation. Proteins were washed three times in TCA (5%), rinsed in ice-cold acetone and re-dissolved in PBS. The amount of radiolabel released from the proteins (ie. not TCA precipitable) after incubation at 37° C. with DTT (1 mM) and SDS (2%) with DTT (DTT/SDS) was determined by Liquid Scintillation Counting (LSC). Cell proteins were also incubated with pronase (2 mg/mL) for 48 hours in 100 µM Tris HCl buffer pH 8 containing 20 mM $CaCl_2$ g at 37° C. or in HCl (12 M) for 12 hours and the release of radiolabel quantified relative that of buffer alone (for pronase) or water (for HCl). All protein samples were processed in triplicate.

Recovery of Incorporated BMAA from Proteins Following Hydrolysis

After incubation with $^3$H-BMAA or cold BMAA, cells were washed three times with PBS, lysed by freeze thawing in Triton-X-100 (0.1%) and cell proteins precipitated in TCA (5%). Protein pellets were washed three times with TCA (5%) and hydrolysed in boiling 6 M HCl at 110° C. for 16 hours as previously described (Mondo, et al., *Mar Drugs* 10, 509-520 (2012)). Protein pellets were freeze-dried and reconstituted in 20 mM HCl. Particulates were removed by centrifugation through 0.22 µM membranes and the hydrolysate derivatized in AccQ•Tag (Waters Corporation, Australia). Amino acids were separated on a Waters C-18 column using a method and gradient as described previously (Mondo, et al., *Mar Drugs* 10, 509-520 (2012)). For recovery of radiolabel in hydrolysed samples, fractions were collected manually every minute for 40 minutes, diluted into 5 ml scintillant (Ultima Gold™ scintillant, Perkin Elmer) and distintegrations per minute (DPM) determined by LSC.

Autofluorescence Imaging of Cells

MRC-5 cells were incubated in DMEM supplemented with 300 µM BMAA in the presence or absence of 300 µM L-serine for 96 hours with daily medium changes. Cellular autofluorescence was visualized using an inverted fluorescent microscope (Olympus IX71) as described previously (Dunlop, et al., *Biochem J* 410, 131-140 (2008)).

Lactate Dehydrogenase (LDH) Assay

Lactate dehydrogenase release from cells was determined as described previously (Tang, et al., *Phytother Res* 25, 417-423 (2010)).

Acridine Orange (AO)/Ethidium Bromide (EtBr) Dual-Staining of Cells

MRC-5 cells were incubated in the presence and absence of 500 µM BMAA for 23 hours. After removing the medium, the cells were rinsed once with warm PBS and incubated in a solution of AO/EB then visualised using fluorescent microscopy as described previously (Tang, et al., *Phytother Res* 25, 417-423 (2010)).

Binding of Annexin V to Phosphatidylserine (PS) Exposed on the Plasma Membrane

Late-stage apoptosis or necrosis was measured by simultaneous staining with propidium iodide and Annexin V using the BD Pharminigen™ Annexin V-FITC apoptosis detection kit and flow cytometry performed as described previously (Dunlop, et al., *Biochem J* 435, 207-216 (2010)).

Extraction Methods for Fruit Fly BMAA Analysis

Thirty flies were from each treatment were weighed and sonicated (Fisher Scientific sonic dismembrator model 100; 2 watts for 30 secs) in 10% trichloroacetic acid (TCA 72 µg/µl). TCA extraction was completed in two steps 20 h at 4° C. using one half the TCA volume followed by centrifugation (13 rpm for 3 min, Labnet spectrafuge 16M) and removal of supernatant. This was followed by a second sonication and extraction, 5 hours at room temperature using an equal volume of TCA, followed by centrifugation and removal of supernatant. The supernatants were pooled (with the exception of 50 µl removed from the last extraction) and centrifuge filtered (0.22 µm Ultrafree-MC, Millipore). The remaining protein pellet was transferred to a glass vial and hydrolyzed in 6 M HCl for 16 hours at 110° C. (58 µg/µl). A portion of the pooled TCA extract was also hydrolyzed in an equal volume of 12 M HCl for 16 hours at 110° C. Extracts were diluted and derivatized with 6-aminoquinolyl-N-hydroxysuccinimidyl carbamate (AQC) and analyzed by LC-MS/MS.

Analytical Methods for Fruit Fly BMAA 6-aminoquinolyl-N-hydroxysuccinimidyl carbamate derivates (AQC Waters AccQTag reagent, PN WAT052880) were analyzed using a triple quadrupole instrument (Thermo Scientific Finnigan TSQ Quantum UltraAM, San Jose, Calif.) after separation by a Waters Acquity-UHPLC system with a Binary Solvent Manager, Sample Manager and a Waters AccQTag Ultra column (part #186003837, 2.1×100 mm) at 55° C. Separation was achieved using gradient elution at 0.65 ml/min in aqueous 0.1% (v/v) formic acid (Eluent A) and 0.1% (v/v) formic acid in acetonitrile (Eluent B): 0.0 min=99.1% A; 0.5 min=99.1% A curve 6; 2 min=95% A curve 6; 3 min=95% A curve 6; 5.5 min=90% A curve 8; 6 min=15% A curve 6; 6.5 min=15% A curve 6; 6.6 min=99.1% A curve 6; 8 min=99.1% A curve 6. This gradient provided separation of BMAA (Irvine Chemistry, Calif.) from isomers 2,4-diaminobutyric acid (Sigma #32830 St. Louis, Mo.) and N-2(amino)ethylglycine (TCI America (Portland, Oreg.). Nitrogen gas was supplied to the heated electrospray ionization (H-ESI) probe with a nebulizing pressure of 40 psi and a vaporizer temperature of 400° C.

The mass spectrometer was operated under the following conditions: the capillary temperature was set at 270° C., capillary offset of 35, tube lens offset of 110, auxiliary gas pressure of 35, spray voltage 3500, source collision energy of 0, and multiplier voltage of −1585. The second quadrupole was pressurized to 1.0 mTorr with 100% argon. Product-ion analysis of AQC derivatized BMAA used m/z 459 (ionized with a single charge) and m/z 230 (ionized with a double charge) as the precursor ions for collision-induced dissociation (CID).

Two-step mass filtering was performed during selective reaction monitoring (SRM) of BMAA after CID in the second quadrupole, monitoring the following transitions: m/z 459 to 119, CE 21 eV; m/z 459 to 289 CE 17 eV; m/z 459 to 171 CE 38 eV; m/z 459 to 258 CE 21 eV; m/z 230 to 171 CE 21 eV. Product ions were detected within the third quadrupole and their relative abundances were quantified.

Identification of BMAA was confirmed by comparison with an authenticated standard (Irvine Chemistry, Calif.) based upon four parameters (a) the presence of the parent ions m/z 459 and m/z 230; (b) retention time; (c) presence of product ions from collision-induced dissociation (transition m/z 459 to 171 quantifier ion; transitions m/z 459 to 289, 258, and 119 qualifier ions; and transition m/z 230 to 171 qualifier ion); (d) ratios of qualifier ions relative to the quantifier ion from parent ion m/z 459. The adequacy of the AQC reaction was monitored by the examination of L-lysine (Sigma #L5501) comparing peak areas of single derivatized lysine (m/z 317) with those of double derivatized lysine (m/z 487).

Example 2

This example describes data indicating that BMAA is incorporated into proteins, which can lead to protein misfolding/aggregation, and which incorporation and misfolding/aggregation is inhibited by L-serine.

Figure 1B:
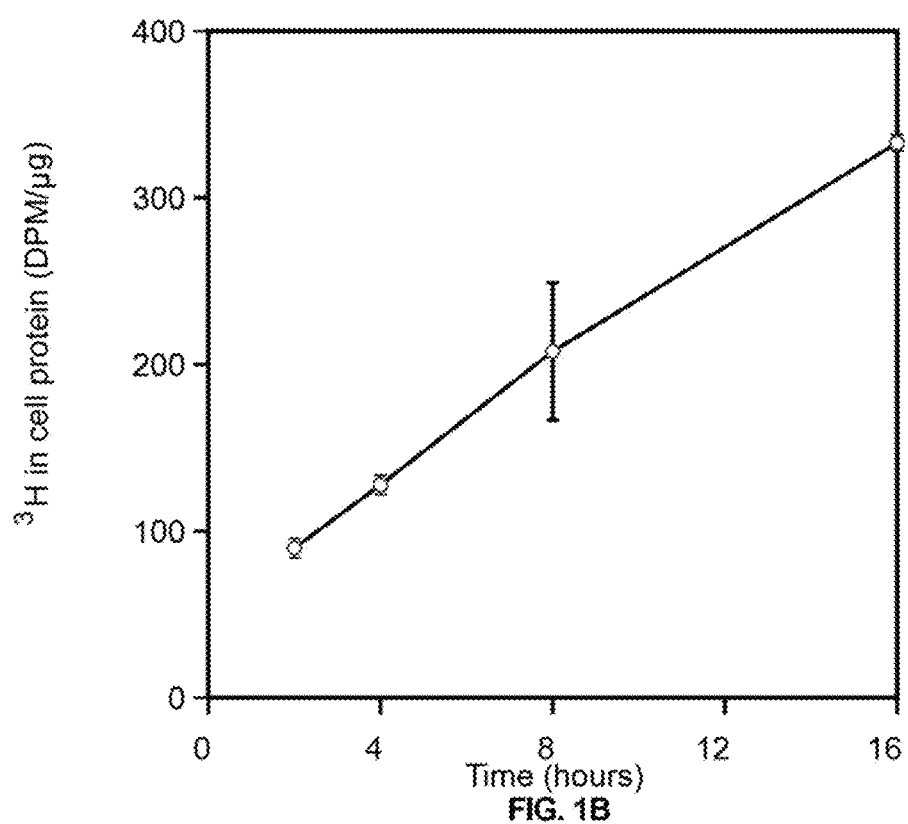
Figure 2:
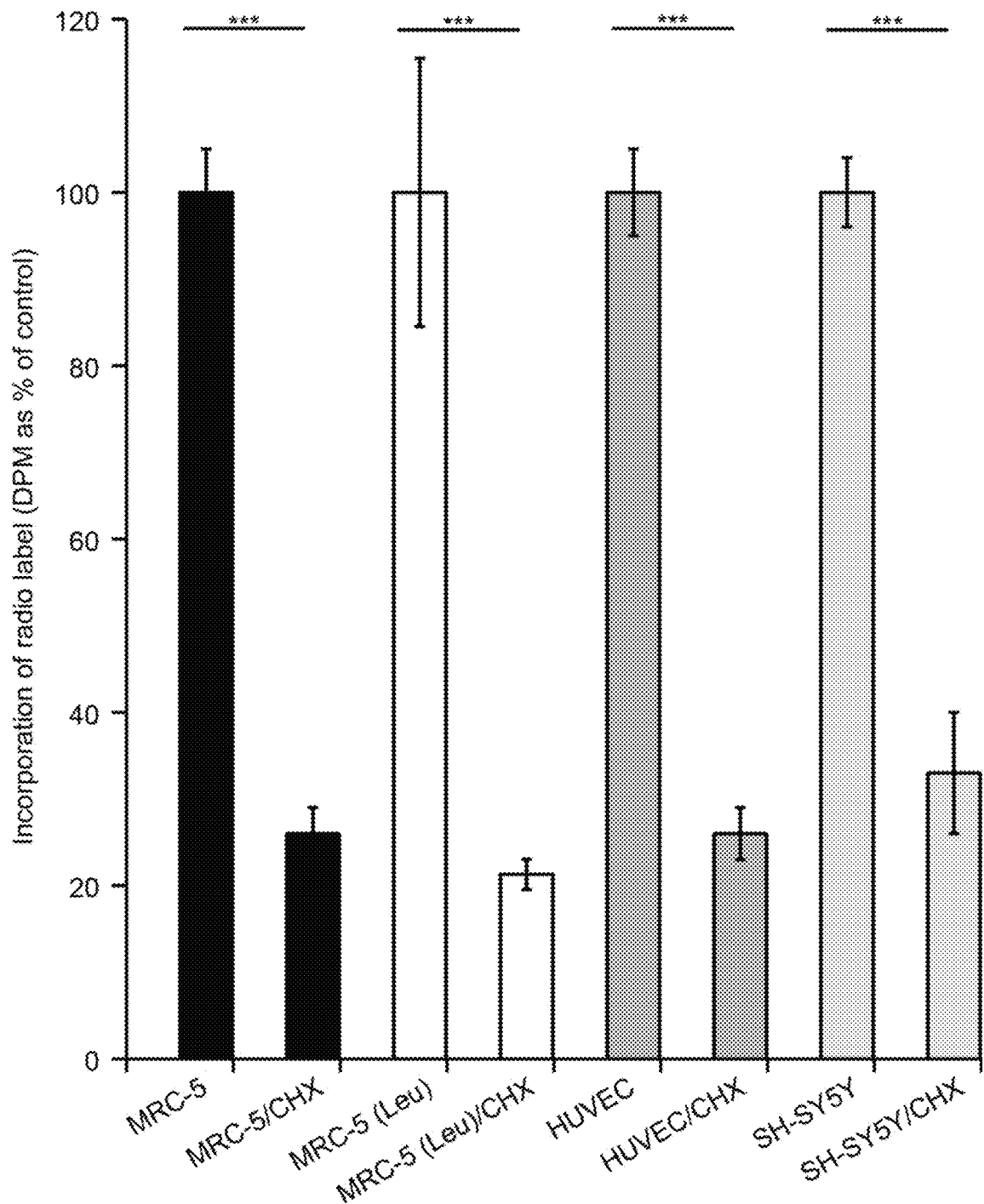
FIG. 2 shows inhibition of incorporation of radiolabel into cell protein by cycloheximide (CHX). MRC-5, HUVEC and SH-SY5Y cells were incubated with $^3$H-BMAA (31.25 nM) with or without CHX 2 µg/ml for 16 hours. Cells proteins were isolated and the amount of radiolabel present in cell proteins expressed as DPM per cell protein. The amount of radiolabel present in cell proteins in the CHX-treated cultures was expressed relative to that of control cultures (no CHX) which was set at 100%. Parallel cultures of MRC-5 cells were incubated with $^3$H-leucine (41 nM) with or without CHX 2 µg/ml [MRC-5 (Leu)] and effects of CHX similarly determined (open bars). *** indicates P<0.001 using Student's two-tailed t-test.

Incubation of human MRC-5 fibroblasts with $^3$H-BMAA in culture medium depleted in amino acids resulted in a time-dependent increase in radiolabel in cell lysates (FIG. 1A), a proportion of which was associated with cell proteins (FIG. 1B). Co-incubation of MRC-5 cells with $^3$H-BMAA along with the protein synthesis inhibitor CHX significantly reduced the amount of radiolabel in the protein fraction (FIG. 2). CHX inhibited incorporation of the protein amino acid $^3$H-leucine into proteins to the same extent as $^3$H-BMAA (FIG. 2) suggesting that $^3$H-BMAA was incorporated into proteins by a protein synthesis-dependent mechanism. $^3$H-BMAA was also found to be protein associated after incubation with human primary endothelial cells (HUVEC) and human neuroblastoma cells (SH-SY5Y), this process was again found to be protein synthesis dependent since it was inhibited by CHX (FIG. 2).

Figure 3:
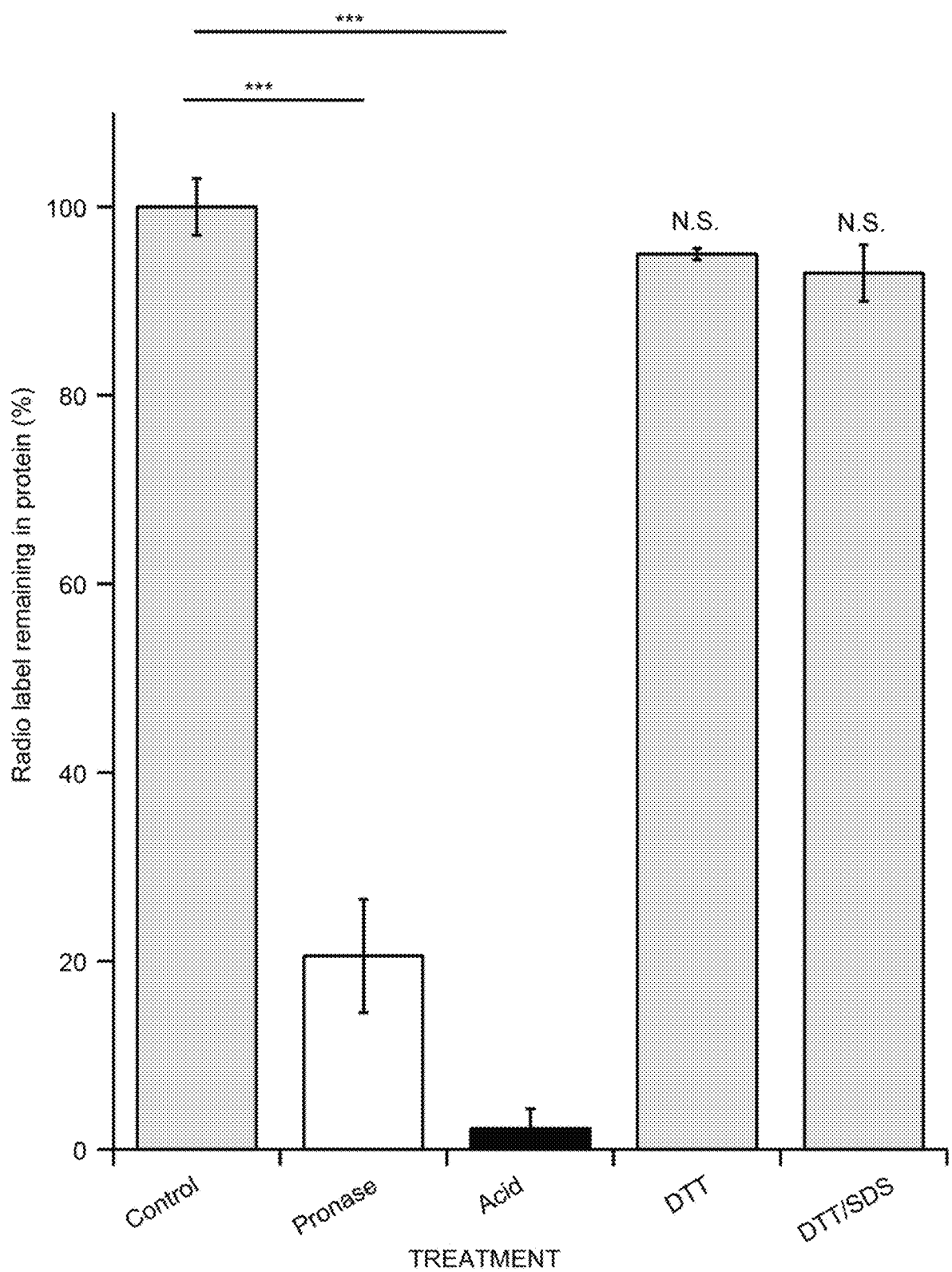
FIG. 3 shows removal of radiolabel from cell proteins following incubation of cells with $^3$H-BMAA. SH-SY5Y cells were incubated with $^3$H-BMAA (31.25 nM) for 24 hours. Cell proteins were isolated by TCA (5%) precipitation. The amount of radiolabel released from proteins (ie. not TCA precipitable) after incubation at 37° C. with DTT (1 mM) and SDS (2%) with DTT (DTT/SDS) are shown relative to that of control samples incubated with buffer alone. Cell proteins were also incubated with pronase (2 mg/ml) for 48 hours at 37° C. or HC1 (12 M) for 12 hours and the release of radiolabel quantified relative that of buffer alone (for pronase) or water (for HC1). All protein samples were processed in triplicate.

To further examine the association between BMAA and cell proteins, availability of a range of treatments to release radiolabel from cell proteins was analyzed. Radiolabelled cell proteins were generated by incubating SH-SY5Y cells with $^3$H-BMAA for 24 hours. The radiolabel could not be removed from the isolated cell proteins by incubation with a 100 fold molar excess of the reducing agent dithiothreitol (DTT) or by heating with the detergent sodium dodecylsulphate (SDS) as well as DTT (FIG. 3). Release of radiolabel required cleavage of peptide bonds by either acid hydrolysis or proteolytic digestion with pronase (FIG. 3).

Figure 4A:
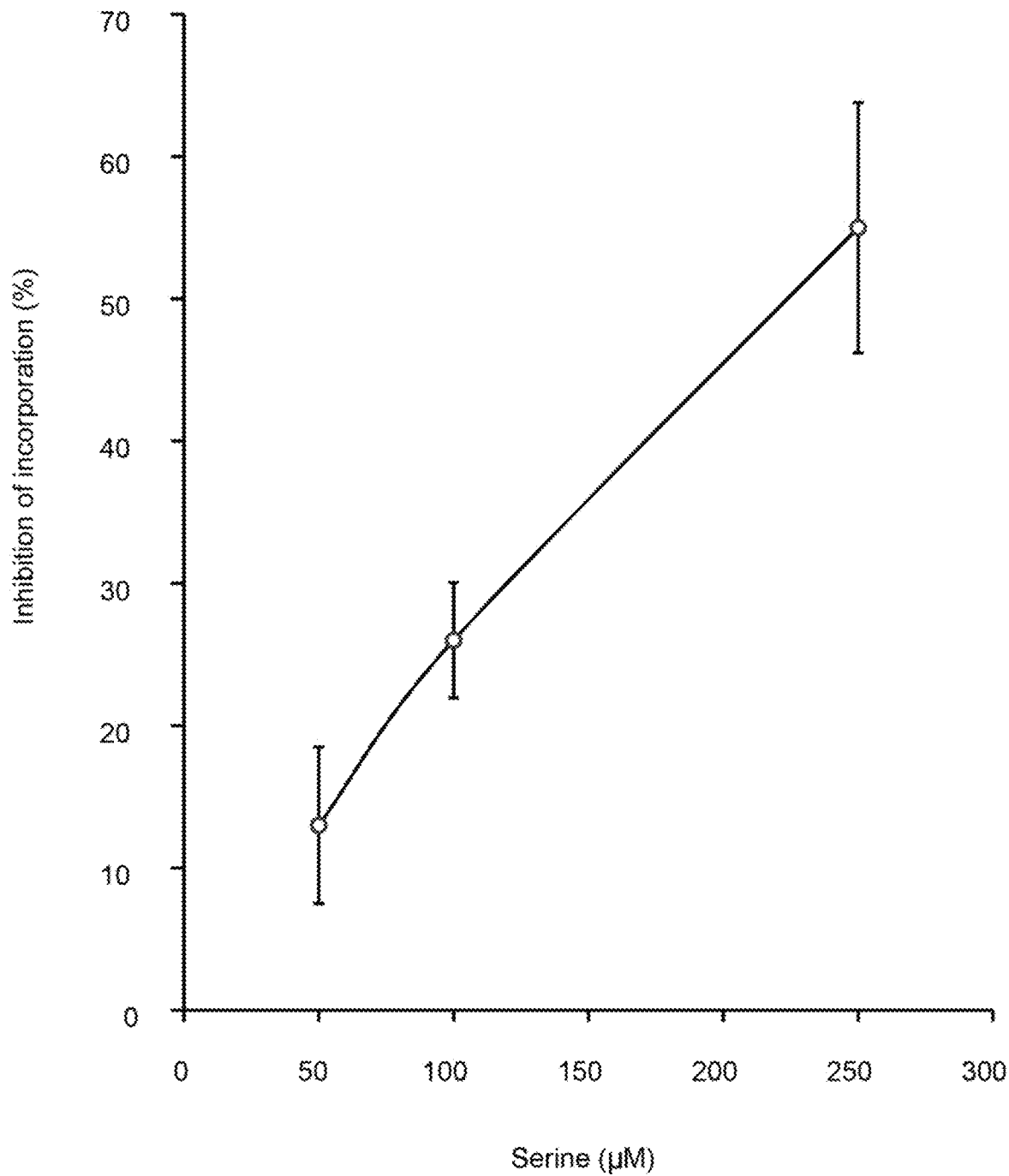
FIGS. 4A-4C show inhibition of incorporation or radiolabel into cell proteins by L-serine. 4A: MRC-5 cells were incubated with $^3$H-BMAA (31.25 nM) for 16 hours in the presence of L-serine (0, 50, 100 and 250 µM). Cell proteins were isolated by TCA precipitation and radiolabel in cell proteins expressed as disintegrations per minute (DPM) per µg cell protein. Inhibition of incorporation of radiolabel at each L-serine concentration is shown relative to cells cultured in medium containing no L-serine. 4B: MRC-5 cells were incubated with 3H-BMAA (31.25 nM) for 16 hours in the presence of 250 µM L-Serine (L-SER) or 250 µM D-serine (D-SER) and the incorporation of radiolabel compared to cells cultures with no L-serine (CTR, set at 100%). 4C: MRC-5 cells were incubated with $^3$H-BMAA (31.25 nM) for 16 hours in the presence of all 20 protein amino acids at 400 µM (NONE), or Hank's buffered salt solution containing no amino acids (ALL) or in presence of all 19 protein amino acids with L-serine omitted (L-SERINE) and the radiolabel in cell proteins expressed as disintegrations per second (DPM).
Figure 4B:
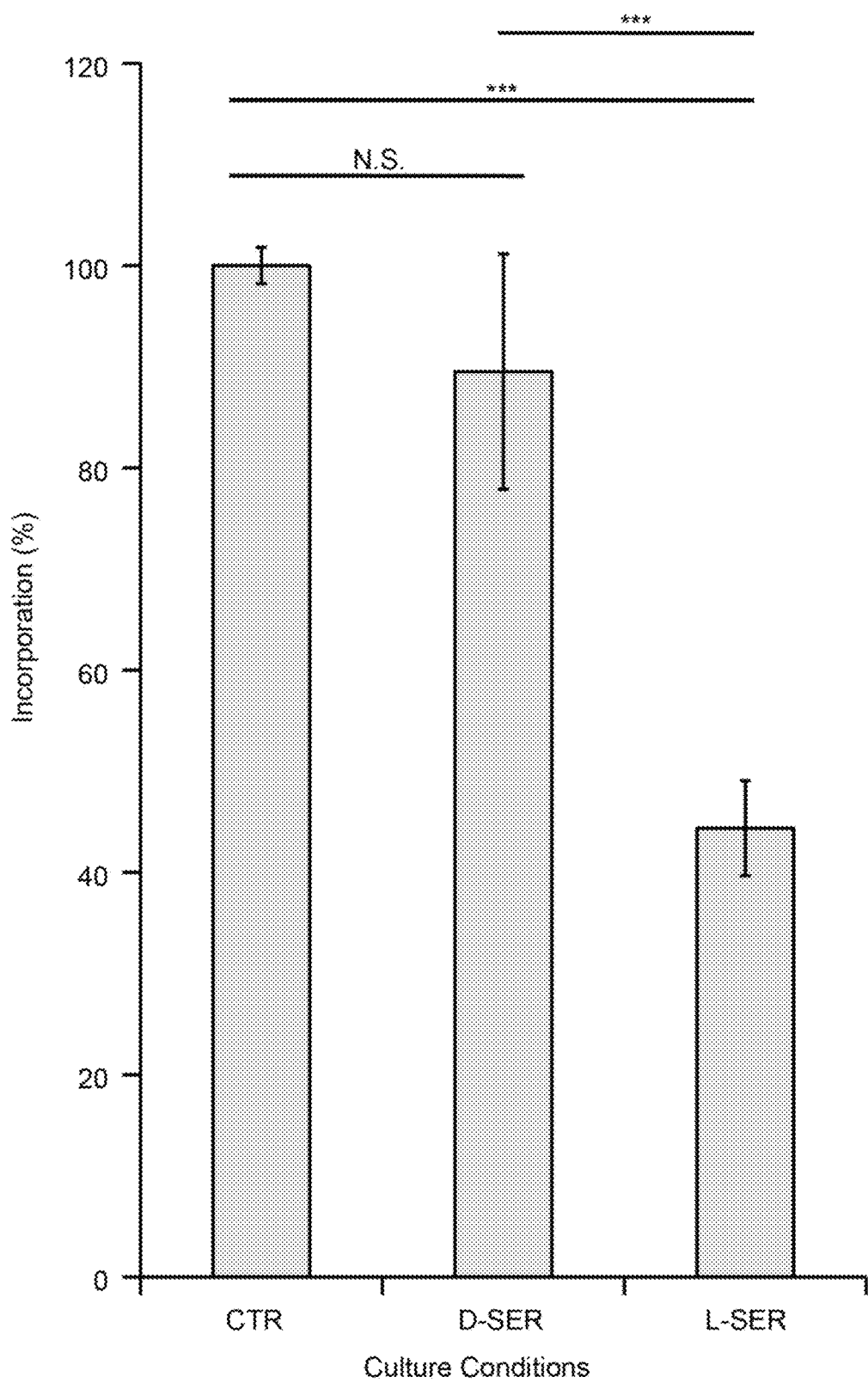
Figure 4C:
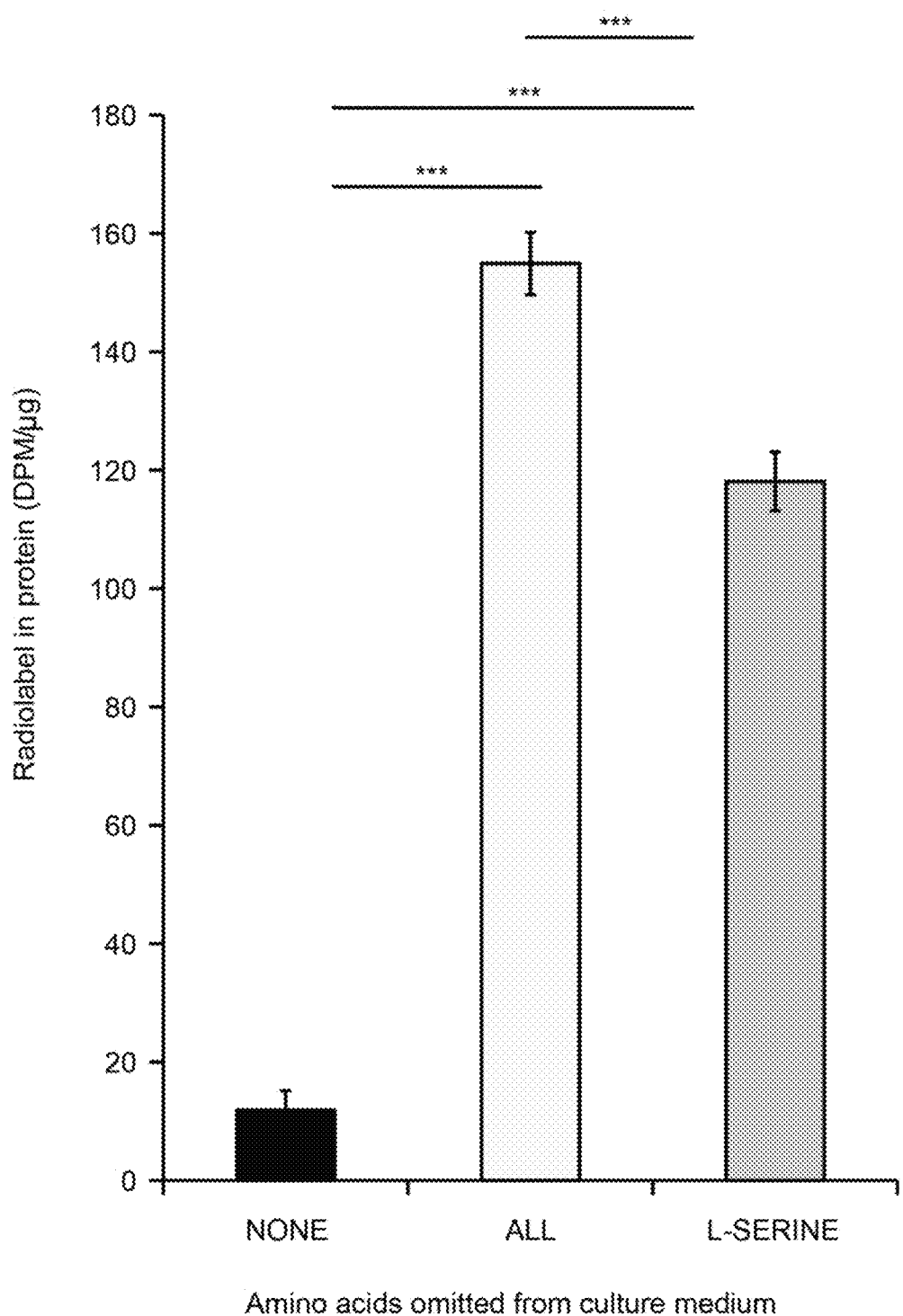

To determine which amino acid was being replaced by BMAA competition between all 20 protein amino acids and $^3$H-BMAA for incorporation into cell proteins was analyzed. Incorporation of $^3$H-BMAA into cell proteins was inhibited in the presence of L-serine in a concentration-dependent manner (FIG. 4A). D-serine, which is not charged by mammalian tRNA synthetases, did not prevent incorporation of $^3$H-BMAA into protein (FIG. 4B). Incubation of cells with $^3$H-BMAA in culture medium which contained all 20 protein amino acids (400 µM) greatly reduced the amount of radiolabel in the protein fraction relative to amino acid-depleted culture conditions (FIG. 4C); when L-serine was omitted from the amino acid mixture, incorporation of BMAA into proteins significantly increased (FIG. 4C).

Figure 5:
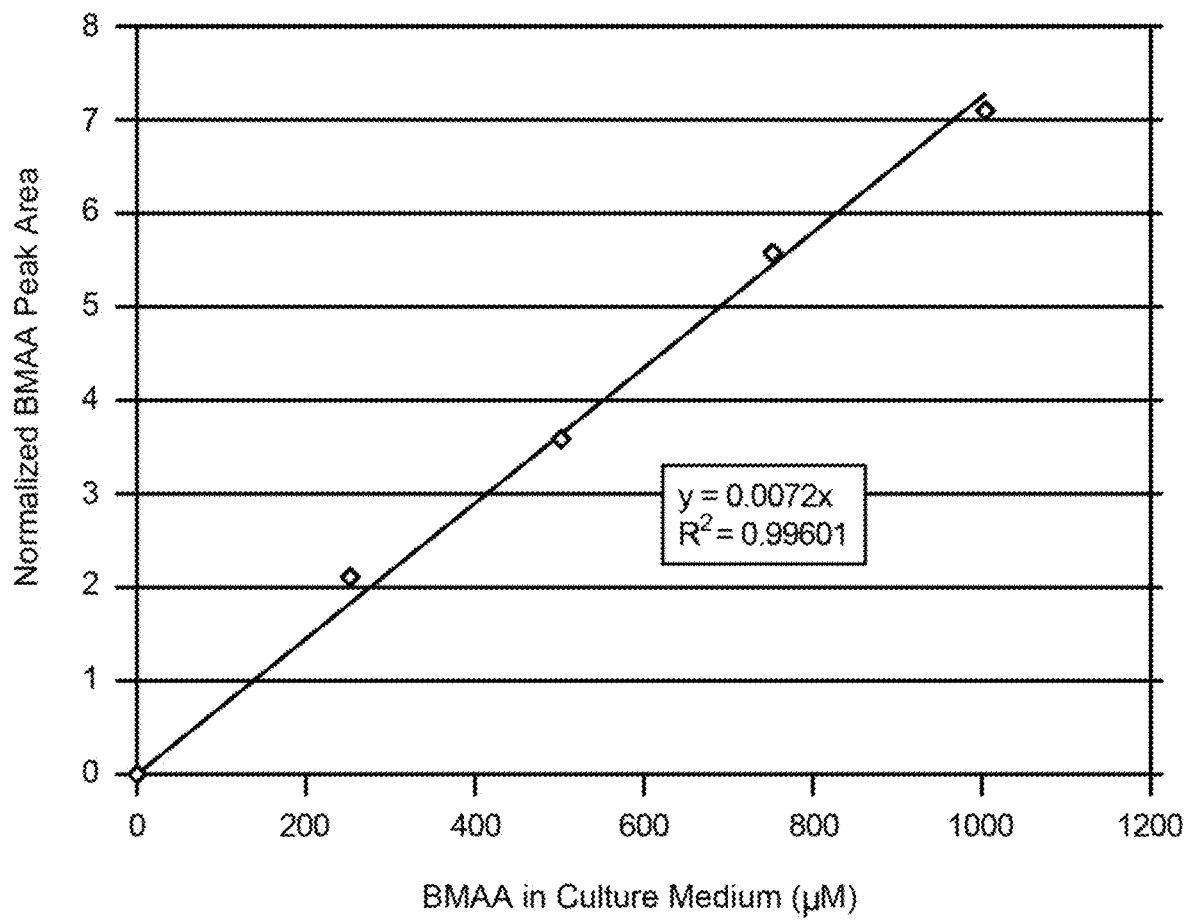
FIG. 5 shows protein-bound BMAA in MRCS cells incubated with free-BMAA in the culture medium. Peak normalized by concentrations of lysine.
Figure 6A:
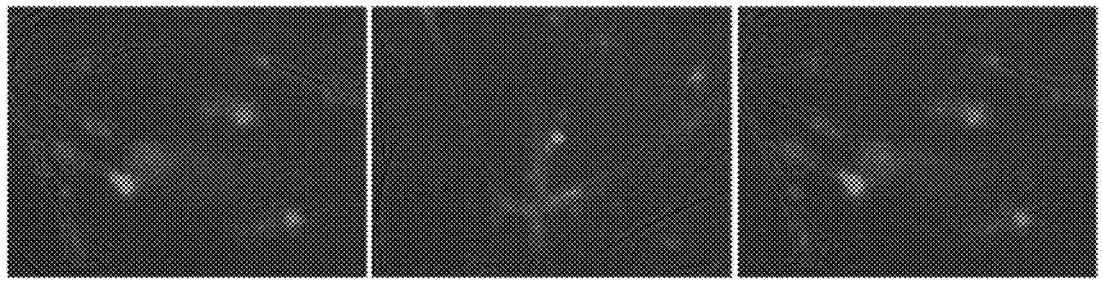
FIGS. 6A-6D show incubation with BMAA results in the formation of autofluorescent bodies and apoptotic changes in cells. Autofluorescence was observed in MRC-5 cells incubated with BMAA (300 µM) for 96 hours (6A) and this was prevented by co-incubation with L-serine (300 µM) (6B). Fluorescent microscopy of MRC-5 cells dual-stained of with acridine orange to detect apoptosis and ethidium bromide to detect necrosis, revealed morphological changes in BMAA-treated cell and the appearance of "pale" cells indicative of cells undergoing apoptosis (6D) which were absent in cells that were not exposed to BMAA (6C). There was a significant increase in Annexin V staining in SH-SY5Y cells incubated with 500 μM BMAA alone showed as measured using flow cytometry. Co-incubation with CHX (2 μg/mL) or L-serine (50 μM) significantly reduced Annexin V binding to cells, indicative of a reduction in apoptosis (6E).

To further confirm that BMAA was present in cell proteins and incorporation was inhibited by L-serine, MRC-5 cells were incubated with a range of concentrations of BMAA (250-1000 µM) or BMAA with L-serine (250-1000 µM) and hydrolysed cell proteins were analyzed by tandem mass spectroscopy on a triple quadrupole LC/MS/MS. Retention times, unique daughter ions, and ratios of m/z transitions during collision-induced dissociation matched those of an authenticated BMAA standard (FIG. 5A). Incubation of cells with increasing concentrations of BMAA resulted in increasing recovery of BMAA from the hydrolyzed proteins (FIG. 5B). Consistent with the studies utilizing $^3$H-BMAA, incorporation of non-labeled BMAA was inhibited by both L-serine and CHX (FIG. 5C). In cells incubated for 96 hours with BMAA (300 µM), autofluorescent bodies were evident in the nucleus, cytosol and in the perinuclear space (FIG. 6A). This is consistent with the accumulation of aggregated proteins, since fluorescent pigment has been shown to accumulate in cells as a result of aging (lipofuscin) or from a range of pathologies associated with impaired proteolysis (ceroid).

Figure 6B:
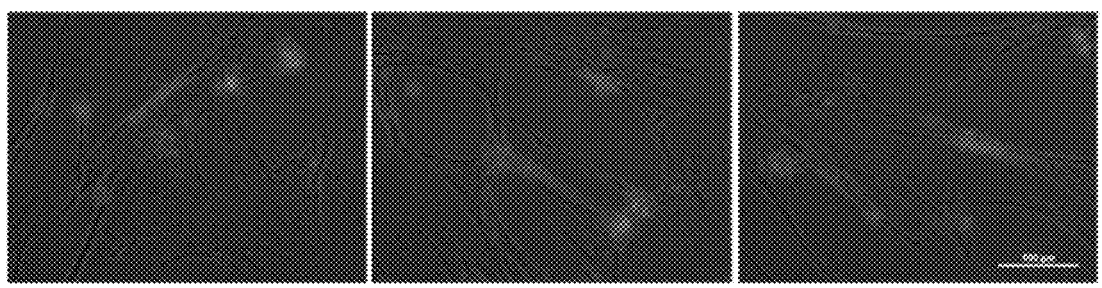
Figure 6C:
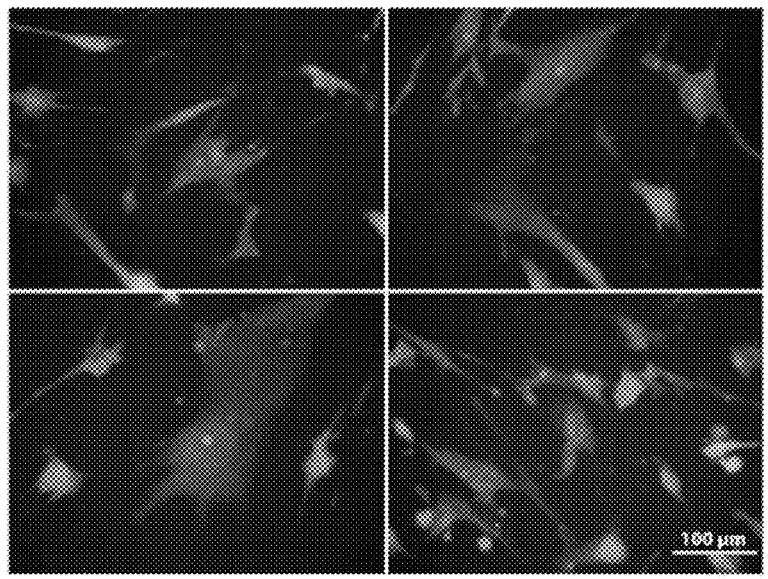
Figure 6D:
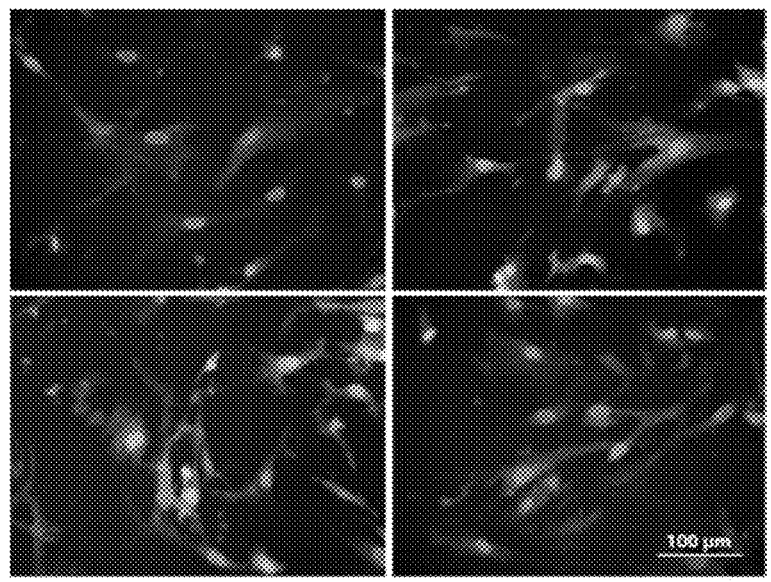
Figure 6E:
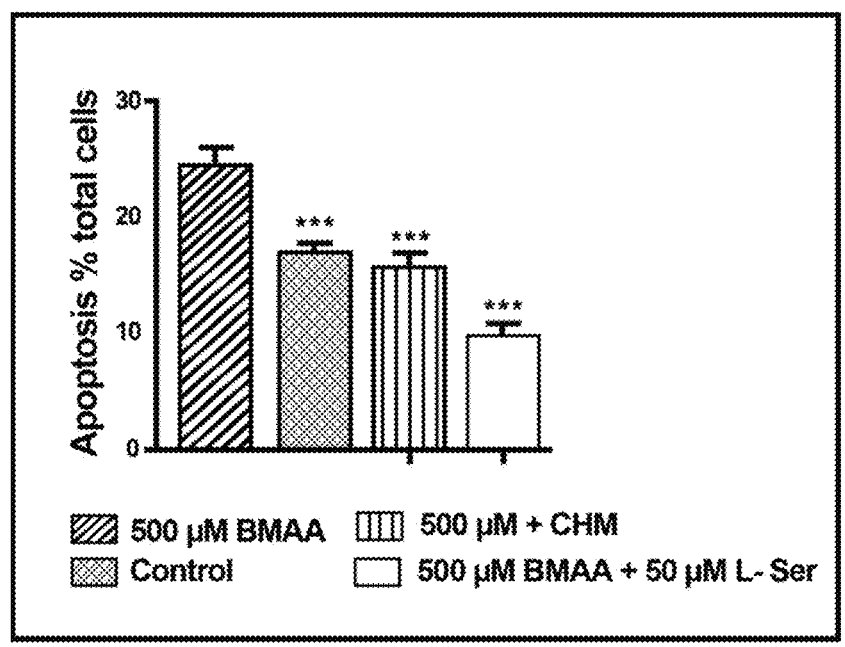

Co-incubation with L-serine prevented the formation of autofluorescent bodies (FIG. 6B). MRC-5 and SH-SY5Y cells did not show signs of necrosis as evidenced by no significant changes in LDH release (data not shown?—it's not) however, apoptosis was present as indicated by increased staining for Annexin V (FIG. 6E) and the increased number of "pale" appearance of cells treated with acridine orange and ethidium bromide (FIGS. 6C and D). Apoptosis could be abrogated by co-incubation with L-serine as well as by CHX, which provides further evidence that this process is dependent upon BMAA incorporation into the protein chain (FIG. 6E). Taken together these data suggest that incorporation of BMAA into cell proteins is a protein synthesis-dependent process, which is inhibited by L-serine.

Based on the foregoing data, the ability of BMAA to be mistakenly incorporated into proteins in place of L-serine would increase misfolding of aggregate-prone proteins. Post-mitotic cells such as neurons would be most affected since, amongst other factors (Polymenidou, et al., *J Exp Med* 209, 889-893 (2012)), they are unable to distribute protein aggregates amongst daughter cells. By promoting misfolding of a number of disease-specific proteins, BMAA could be therefore be a single trigger for the complex neurological disorders reported on Guam in which amyotrophic lateral sclerosis, Parkinson's disease and dementia-like symptoms were evident in individuals exposed to BMAA (Bradley, et al., *Amyotroph Lateral Scler* 10 Suppl 2, 7-20 (2009)).

Example 3

This example describes data indicating that L-Serine rescues *Drosophila melanogaster* (fruit flies) from BMAA induced mortality, and additional useful models.

APP is evolutionarily conserved from invertebrates to vertebrates. This allows research to be performed on APP in *Drosophila* fruit flies, to study human diseases such as Alzheimer's disease. The *Drosophila* model was used to characterize how BMAA influences the production of the APP-derived fragments, especially the amyloidogenic fragments. The *Drosophila melanogaster* (fruit fly) insect model is a convenient invertebrate system to measure important features of a human disease, including plaque formation, memory loss, social interactions, and the overall neuronal structure of a model organism. Fruit flies also engineered to produce extra human Aβ will be fed BMAA and the resulting increase or decrease in plaque inducing Aβ will be measured. Flies are an excellent model because their genetic characteristics have been well-worked out and a whole host of human diseases are examined in fruit flies.

Figure 7:
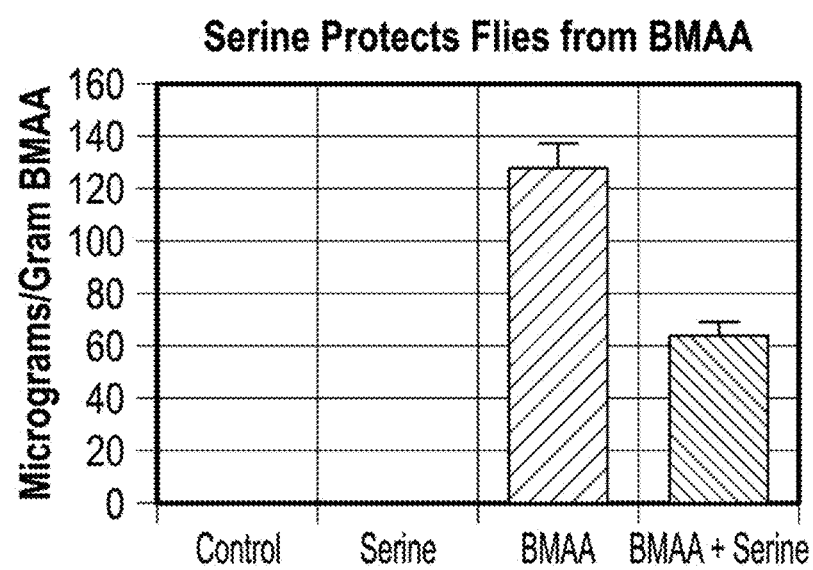
FIG. 7 shows that L-serine reduces BMAA incorporation into proteins.

Preliminary studies show the ability of L-Serine to prevent misincorporation of BMAA into proteins. In a series of feeding experiments, Drosophila fruit flies were fed four different types of media: 1) standard fruit fly media with 0 mM BMAA (control), 2) media enriched with 25 mM L-Serine, 3) media with 25 mM BMAA added, and 4) media with both 25 mM BMAA and 25 mM L-Serine added for three days of feeding. Misincorporation of BMAA into proteins was then analyzed using triple quadrupole LC/MS/ MS and Orbital Trap LC/MS/MS. Addition of L-Serine to the media reduced by half the amount of BMAA misincorporation (FIG. 7).

Figure 8:
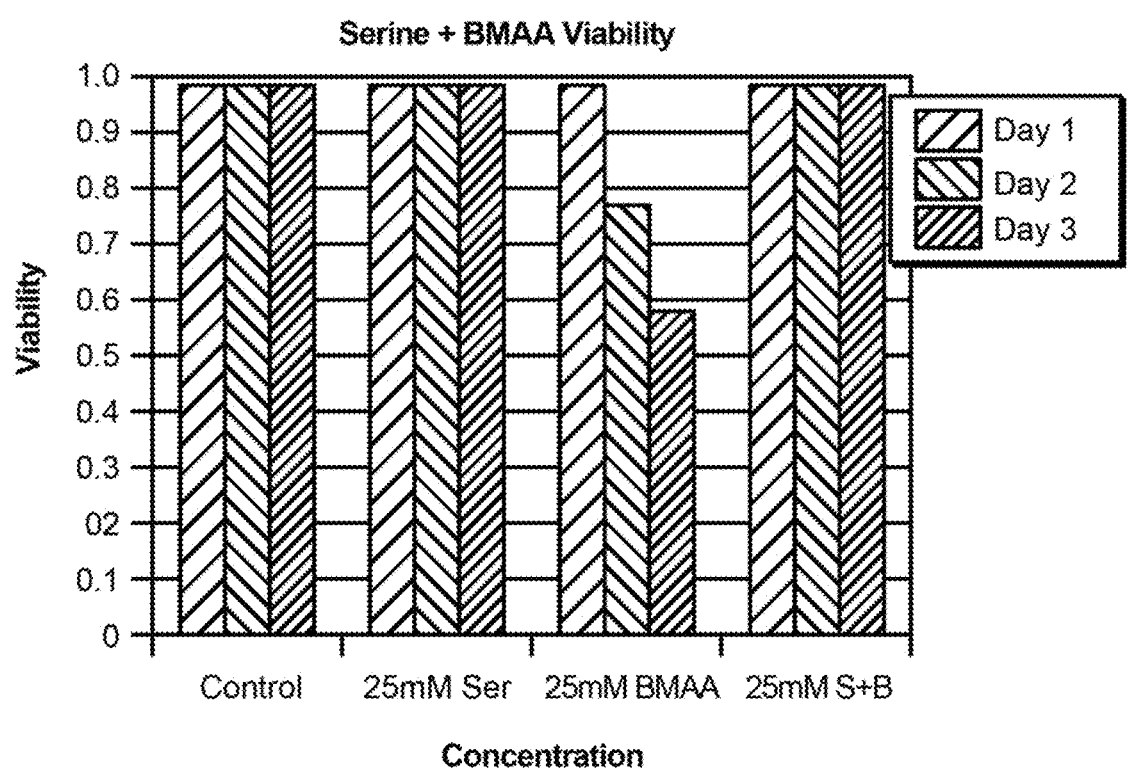
FIG. 8 shows that L-serine promotes Drosophila survival and blocks BMAA induced mortality.

Equally interesting is the analysis of the protective value of L-Serine on Drosophila dosed with BMAA. Fruit flies fed with BMAA enriched media (third set of blocks) suffered a 40% mortality after three days, while flies fed with Serine plus BMAA (fourth set of blocks) had no mortality (FIG. 8). These flies were rescued by L-Serine.

There are two additional models that will be used to study the effects of BMAA as follows:

1. Human neuronal cell lines (NT2 cells). These human neurons are cultured in petri dishes and are robust enough to study for long periods of time. These cells are the closest model to what may occur at the neuronal level in the human brain. The ex-vivo cells carry all the features important for neuron to neuron communication, neurotransmitter glutamate function and a convenient system for measuring cell viability and APP-fragments using protein (Western blot) techniques.

2. Highly proliferating cells, denoted CHO/APP cells. These cells, derived from hamsters, have extra amounts of APP which will enable measurement of smaller Aβ fragments. Often, protein techniques while good at detecting small fragments, are further enhanced by using cells lines that have been engineered to produce more of a particular protein, in this case, APP.

Example 4

This example describes data in a vertebrate model that illustrates neurotoxicity of BMAA and that BMAA causes abnormalities in neuronal development.

The zebrafish (*Dario rerio*) is a clinically relevant model for human neurological disorders and diseases such as spinal muscular atrophy, ataxia, amyotrophic lateral sclerosis (ALS), epilepsy, Huntington's disease, Parkinson's disease, dementia and Alzheimer's disease (see, e.g., Kabashi et al., *Trends Genet.* 26:373 (2010); and Kabashi et al., *Bicohim. Biophys. Acta* 1812:335 (2011)). Zebrafish was used to determine BMAA toxicity, and to assess functional changes in swimming performance in fish following a single exposure to BMAA.

BMAA was directly injected through the chorion into the yolk, allowing it to directly compete with L-serine for incorporation into newly synthesised proteins in the developing fish. BMAA (100 mg/ml in water) or water were delivered by an automated Picospritzer pump set to deliver 5 nL per injection into the yolk (−110 μl) of zebrafish immediately after being fertilized. Fish were left to develop for 30 hours in standard conditions.

Survival: In the control group 91% of the fish survived. In the BMAA-treated group, zebrafish viability was reduced to 74%.

Surviving fish were reared in an aquarium equipped with biological filtration and temp control set at 28° C. for 3 months. BMAA-treated and control fish from the same parents were reared in the same tanks, then separated based on fluorescent tag prior to swimming assessment. After 3 months all healthy adult fish with no deformations or abnormalities were examined. Critical swimming speed was determined, defined as the maximum swimming velocity that can be sustained for a set period in a water tunnel. Water was pumped from as reservoir (EcoTech Marine MP10 Vortech Propeller Pump with EcoSMART Driver) through 50 mm diameter tubing. A mesh screen located in the downstream end prevented fish from leaving the test section. Fish were swum for 6 minutes at setting 4 on the pump, then speed incrementally increased to setting 6 and maintained until fish failed.

Figure 9:
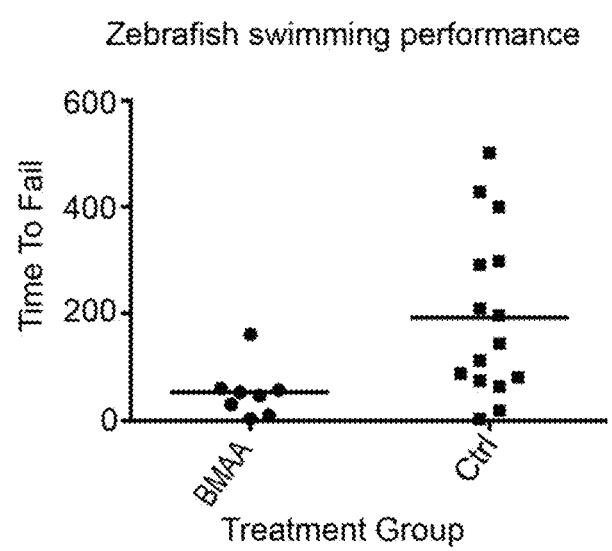
FIG. 9 shows that BMAA impairs zebrafish swimming performance.

Swimming performance: BMAA-treated fish showed a significant impairment in swimming performance compared to the control fish (Ctrl) based on the time to fail (seconds) (FIG. 9). There was a significant difference between the two groups ($p<0.001$)

Figure 10A:
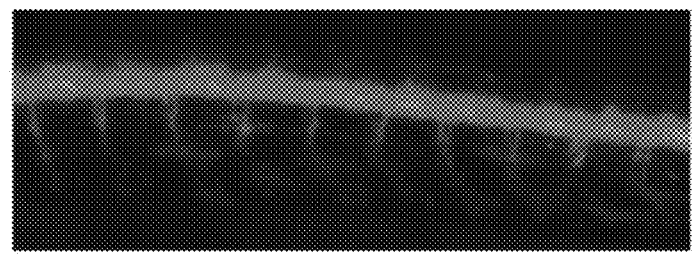
FIGS. 10A-10C show that BMAA injection causes abnormalities in neuronal development. 10A: growth and branching of motor neurons was clearly observed after 30 hours. 10B and 10C: In eggs injected with L-BMAA, truncated neurons (indicated by white arrows) were observed.
Figure 10B:
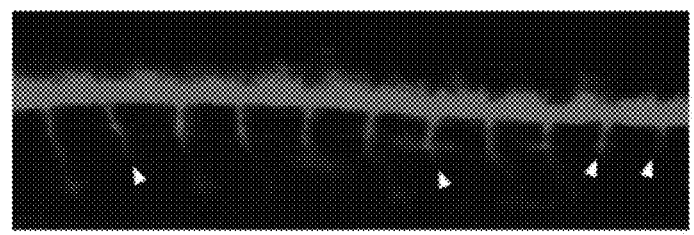
Figure 10C:
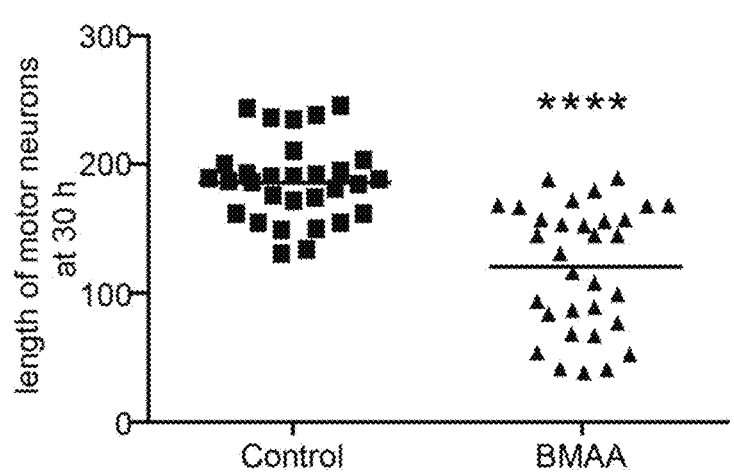

Neuronal development: Neurons were observed under a fluorescent microscope. In control injected fish (FIG. 10A), growth and branching of motor neurons could be clearly observed after 30 hours. In eggs injected with L-BMAA, truncated neurons were observed (FIG. 10B, indicated by white arrows). The difference in total motor neuron length was quantitated by measuring the first ten motor neuron projections marked before the end of the yolk extension (Paquet D et al., *J. Clin. Invest.* 119:1382 (2009)). Measurements were conducted in three different fish per treatment using the freehand line tool in ImageJ (http://rsb.info.nih.gov/ij/ Version 1.46r). Data was collated in GraphPad Prism (version 6 for OSX) and statistical significance calculated using a Student's T-test. Horizontal lines represent means of neuron length within and between samples (FIG. 10C). $P<0.0001$.

Example 5

This example describes analysis of L-Serine prevention of BMAA misincorporation into rodent neuroproteins.

A series of studies were conducted which demonstrated that radio-labeled BMAA, both triated and 14-C labeled BMAA, rapidly cross the blood-brain barrier in rats and are inserted into neuroproteins. Studies testing to determine if L-Serine blocks the misincorporation of radio-tagged BMAA into rodent brains are undertaken.

Example 6

This example describes a Vervet model for evaluating the protective effect of L-Serine against progressive neurodegenerative disease.

Non-human primates are exceptional models for understanding human disease, since these animals share a large portion of the human genome and have significant homologies with human nervous systems. African green monkeys, known as vervets, are known to carry the APOe gene and develop cerebral amyloid-beta (Aβ) plaques, making vervets a promising model for Alzheimer's disease (AD). One vervet study and one study found that Aβ vaccinations reduced Aβ in the brain. A subsequent human phase I trial showed that the Aβ vaccinations were safe for people and this avenue is currently being investigated largely due to the positive trials in vervets, indicating that vervets are an accepted model for human Alzheimer's.

A colony of vervets was studied for protein misfolding and protein aggregates produced by oral administration of BMAA and the ability of equivalent doses of L-Serine to prevent BMAA misincorporation into proteins, as well as L-serine to prevent protein misfolding and protein aggregates. Vervets (16 animals) were divided into four different groups. Four of the vervets were fed 651 mg of BMAA daily. A second group of four vervets were fed 651 mg of BMAA plus 651 mg of L-Serine each day. The third group was dosed with 651 mg of L-Serine daily, and the fourth control group received placebos, in this case 651 mg of rice flour. These doses, which normalize to 210 mg/kg/day, are comparable to the doses used for macaques that induced acute neurotoxicity in some animals with profound movement and cognitive deficits in the dosed animals.

Neuroproteins derived from the vervet tissues as well as blood plasma and cerebral spinal fluid samples are being analyzed with orbital trap mass spectrometry and triple quadrupole mass spectrometry for evidence of BMAA misincorporation. In addition, the neuroproteins are studied for evidence of misfolding and aggregation using stains and fluorescent microscopy as previously detailed, as well as gross neuropathological studies of brain tissues for lesions or other neuroanatomical adnormalities.

Example 7

This example describes studies to evaluate Alzheimer's brains for proteins that have BMAA misincorporated into the protein.

Differences in the abundance of the enzymes, particularly 3-PGDH, PSAT, and PSPH that make endogenous L-Serine within primate astrocytes in the neuronal system body will be examined in order to understand if deficiencies in neuronal L-Serine makes neuroproteins more vulnerable to BMAA-misfolding. The specific make up of these Alzheimer's-related proteins can be used to prove that BMAA is being misincorporated in place of L-Serine in living primate nervous systems. At the conclusion of these in vivo studies, a determination if L-Serine prevents misincorporation of BMAA into neuroproteins, and if L-Serine is able to prevent subsequent protein misfolding and aggregation.

Extracts from Alzheimer's brains to purify and analyze for proteins that have had BMAA misincorporated into the protein sequence will be performed. Samples of brains from patients who suffered from Alzheimer's disease are obtained and proteins from the brains extracted. Extracts will be separated by electrophoresis on gels and the proteins transferred to membranes. These membranes containing all the proteins in the extracts will be probed with BMAA antibodies to determine which proteins show reactivity with the antibodies and hence, which proteins contain BMAA. The membrane probing will allow a calculation of the size or molecular weight of these proteins. An isolation of the proteins that have the same molecular weight as for the proteins that were positive when assessed with membranes. These proteins will then be cut out from the gel, digested and analyzed using a mass spectrometer. The sequences obtained for these digested proteins will be assessed using protein analysis software to identify the proteins based on their sequences and to also determine the sites where the misincorporation of BMAA occurs.

Alternatively, BMAA antibodies will be used to purify proteins from solutions by preparing antibody affinity columns. Protein extracts from Alzheimer's brains will be subject to affinity purification. After passing the protein solution through the antibody column, proteins containing BMAA will be more likely to bind to the antibodies on the column and the proteins not containing BMAA will flow through the column. The column will be washed and proteins containing BMAA will be eluted from the column as a semi-pure solution. The use of such columns allows us to rapidly purify protein solutions such that there is a greater likelihood of obtaining proteins containing BMAA. Once isolated, the proteins will be digested using enzymes before analysis of the fragments using mass spectrometry and protein analysis software.

Example 8

This example describes proposed human clinical trials of L-Serine as a treatment for progressive neurodegenerative illness.

Based on the above considerations L-Serine and its structural derivatives are expected to function as both a prophylactic that can prevent human progressive degenerative illness, as well as a treatment that will slow the progression of symptoms in patients who have been diagnosed with progressive neurodegenerative illness.

Human clinical trials will be performed to determine if L-Serine can slow the progression of ALS and Alzheimer's, or possibly even prevent their occurrence. To approve any compound as a drug, the U.S. Food and Drug Administration (FDA) requires three different phases of human clinical trials. Phase I trials typically involve a small number of patients (10-12) with the disease, and are designed to see if the drug is safe and well-tolerated by patients. Phase II trials involve more patients (30-60) and are designed to see if the drug is effective in treating the disease. Phase III trials are designed to reconfirm both safety and efficacy, and to determine possible side effects. These trials typically involve 300-500 patients.

Based on the in vitro and in vivo data previously detailed, it would be unethical to present ALS patients with a placebo in a randomized double-blind clinical trial. Accordingly, historical data on control ALS patients from previous clinical trials conducted by the Phoenix Neurological Associates and others will be used.

In the current design, a Phase I open label trial of 20 ALS patients will receive L-Serine orally at doses ranging from 500 mg/day to 30 g/day for six months. ALS Inclusion Criteria: Age 18-85; Male or Female; clinically diagnosed with probable or definite ALS based on El Escorial criteria; ALS-FRS score >25; and able to provide informed consent to and comply with all medical procedures. ALS Exclusion Criteria: Patients with FVC below 60%; evidence of any MND for over 3 years; any other co-morbid condition that could make completion of trial unlikely; history of intolerance to L-serine; taking any other trial medications; and if female, pregnant or breast-feeding, or if of childbearing age, any unwillingness to prevent pregnancy until trials are completed;

Although the Phase I trial is designed to demonstrate safety of L-Serine dosing for ALS patients, within these dose ranges there could be a possible slowing of the reduction in symptoms by using the ALSFRS-R, a rating of progressive Amyotrophic Lateral Sclerosis based on clinical symptoms. In addition, blood plasma and cerebral spinal fluid samples will be withdrawn and analyzed using triple quadrupole LC/MS/MS and Orbital trap LC/MS/MS to determine degree of BMAA misincorporation in neuroproteins, plasma L-Serine levels. Staining and fluorescent microscopy studies similar to those detailed herein will be used to detect protein aggregates and degree of misfolding of key proteins associated with progressive neurodegeneration. In addition, neuroproteins that are particularly vulnerable to BMAA misincorporation will be identified using orbital trap mass spectrometry.

What is claimed:

1. A method of inhibiting or reducing incorporation of β-N-methylamino-L-alanine (BMAA), 2,4-diaminobutyric acid (2,4-DAB), 2,3-diaminobutyric acid (2,3-DAB), N-(2-aminoethyl)glycine (AEG) or β-N-methyl-alanine (BAMA) into one or more proteins of a mammalian cell in a mammal, the method comprising administering to a mammal in need thereof a pharmaceutical composition consisting essentially of:

(1) an active ingredient selected from the group consisting of L-serine, a salt of L-serine and an L-serine ester; and (2) at least one pharmaceutically acceptable carrier or excipient;

wherein the pharmaceutical composition includes the active ingredient in an amount of from 10 to 50 grams per day, and wherein the active ingredient is sufficient to inhibit or reduce incorporation of β-N-methylamino-L-alanine (BMAA), 2,4-diaminobutyric acid (2,4-DAB), 2,3-diaminobutyric acid (2,3-DAB), N-(2-aminoethyl)glycine (AEG) or β-amino-N-methyl-alanine (BAMA), into the one or more proteins of the mammalian cell.

2. The method of claim 1, wherein the mammal is human.

3. The method of claim 1, wherein the one or more proteins are in the mammal's central nervous system.

4. The method of claim 1, wherein the pharmaceutical composition is administered orally.

5. The method of claim 1, wherein the one or more proteins is TAR DNA-binding protein 43 (TDP-43) or alpha-synuclein.

6. The method of claim 1, wherein the mammal has a neurological disease or disorder selected from the group consisting of Alzheimer's disease, Parkinson's disease, Amyotrophic Lateral Sclerosis (ALS), Progressive Supranuclear Palsy (PSP), Lewy Body Dementia (LBD), Amyotrophic Lateral Sclerosis/Parkinsonism Dementia Complex (ALS/PDC), Huntington's disease (HD), Pick's disease and Frontotemporal Dementia (FTD).

7. The method of claim 6, wherein the mammal has Alzheimer's disease or ALS.

8. The method of claim 1, wherein the incorporation of β-N-methylamino-L-alanine (BMAA), 2,4-diaminobutyric acid (2,4-DAB), 2,3-diaminobutyric acid (2,3-DAB), N-(2-aminoethyl)glycine (AEG) or β-N-methyl-alanine (BAMA) into the one or more proteins of the mammalian cell is the result of binding of BMAA, 2,4-diaminobutyric acid (2,4-DAB), 2,3-diaminobutyric acid (2,3-DAB), N-(2-aminoethyl)glycine (AEG) or β-N-methyl-alanine (BAMA) to a serine aminoacyl-tRNA synthetase.

9. The method of claim 1, wherein the pharmaceutical composition includes the active ingredient in an amount of from 20 g to 40 g per day.

10. The method of claim 1, wherein the pharmaceutical composition includes the active ingredient in an amount of from 30 g to 40 g per day.

11. A method of inhibiting uptake of β-N-methylamino-L-alanine (BMAA), 2,4-diaminobutyric acid (2,4-DAB), 2,3-diaminobutyric acid (2,3-DAB), N-(2-aminoethyl)glycine (AEG) or β-amino-N-methyl-alanine (BAMA) into a cell of a mammal, the method comprising administering to a mammal in need thereof a pharmaceutical composition consisting essentially of:

(1) an active ingredient selected from the group consisting of L-serine, a salt of L-serine and an L-serine ester; and (2) at least one pharmaceutically acceptable carrier or excipient;

wherein the pharmaceutical composition includes the active ingredient in an amount of from 10 to 50 grams per day, and wherein the active ingredient is sufficient to inhibit uptake of β-N-methylamino-L-alanine (BMAA), 2,4-diaminobutyric acid (2,4-DAB), 2,3-diaminobutyric acid (2,3-DAB), N-(2-aminoethyl)glycine (AEG) or β-amino-N-methyl-alanine (BAMA) into the cell of the mammal.

12. The method of claim 11, wherein the mammal is human.

13. The method of claim 11, wherein the cell is a neuron or glial cell.

14. The method of claim 11, wherein the pharmaceutical composition includes the active ingredient in an amount of from 20 g to 40 g per day.

15. The method of claim 11, wherein the pharmaceutical composition includes the active ingredient in an amount of from 30 g to 40 g per day.

16. A method of preventing, inhibiting or reducing misfolding or aggregation of one or more proteins of a mammalian cell in a mammal, the method comprising administering to a mammal in need thereof a pharmaceutical composition consisting essentially of:

(1) an active ingredient selected from the group consisting of L-serine, a salt of L-serine and an L-serine ester; and (2) at least one pharmaceutically acceptable carrier or excipient;

wherein the pharmaceutical composition includes the active ingredient in an amount of from 10 to 50 grams per day, and wherein the active ingredient is sufficient to prevent, inhibit or reduce misfolding or aggregation of the one or more proteins of the mammalian cell.

17. The method of claim 16, wherein the mammal is human.

18. The method of claim 16, wherein the mammal has Alzheimer's disease or ALS.

19. The method of claim 16, wherein the misfolding or aggregation of the one or more proteins of a mammalian cell in a mammal results from incorporation of β-N-methylamino-L-alanine (BMAA), 2,4-diaminobutyric acid (2,4-DAB), 2,3-diaminobutyric acid (2,3-DAB), N-(2-aminoethyl)glycine (AEG) or β-N-methyl-alanine (BAMA) into the one or more proteins of the mammalian cell.

20. The method of claim 16, wherein the pharmaceutical composition includes the active ingredient in an amount of from 20 µg to 40 µg per day.

21. The method of claim 16, wherein the pharmaceutical composition includes the active ingredient in an amount of from 30 g to 40 g per day.

* * * * *